(12) United States Patent
Abolfathi et al.

(10) Patent No.: US 8,023,676 B2
(45) Date of Patent: Sep. 20, 2011

(54) SYSTEMS AND METHODS TO PROVIDE COMMUNICATION AND MONITORING OF USER STATUS

(75) Inventors: Amir Abolfathi, Woodside, CA (US);
John Spiridigliozzi, San Mateo, CA (US)

(73) Assignee: Sonitus Medical, Inc., San Mateo, CA (US)

( * ) Notice: Subject to any disclaimer, the term of this patent is extended or adjusted under 35 U.S.C. 154(b) by 870 days.

(21) Appl. No.: 12/041,100

(22) Filed: Mar. 3, 2008

(65) Prior Publication Data

US 2009/0220921 A1 Sep. 3, 2009

(51) Int. Cl.
*H04R 25/00* (2006.01)
(52) U.S. Cl. .................. 381/326; 381/151
(58) Field of Classification Search .......... 381/312,
381/315, 322, 324, 326, 328, 380, 151; 600/25,
600/300, 301; 607/56, 57; 455/41.2, 100
See application file for complete search history.

(56) References Cited

U.S. PATENT DOCUMENTS

| | | | |
|---|---|---|---|
| 2,045,404 | A | 6/1936 | Nicholides |
| 2,161,169 | A | 6/1939 | Jefferis |
| 2,318,872 | A | 5/1943 | Madiera |
| 2,977,425 | A | 3/1961 | Cole |
| 2,995,633 | A | 8/1961 | Puharich et al. |
| 3,156,787 | A | 11/1964 | Puharich et al. |
| 3,170,993 | A | 2/1965 | Puharich et al. |
| 3,267,931 | A | 8/1966 | Puharich et al. |
| 3,325,743 | A | 6/1967 | Blum |
| 3,787,641 | A | 1/1974 | Santori |
| 3,894,196 | A | 7/1975 | Briskey |
| 3,985,977 | A | 10/1976 | Beaty et al. |
| 4,025,732 | A | 5/1977 | Traunmuller |

(Continued)

FOREIGN PATENT DOCUMENTS

EP 0715838 A2 6/1996

(Continued)

OTHER PUBLICATIONS

Broyhill, D., "Battlefield Medical Information System—Telemedicine," A research paper presented to the U.S. Army Command and General Staff College in partial Fulfillment of the requirement for A462 Combat Health Support Seminar, 12 pages, 2003.

(Continued)

*Primary Examiner* — Huyen D Le
(74) *Attorney, Agent, or Firm* — Levine Bagade Han LLP

(57) ABSTRACT

An electronic and transducer device can be attached, adhered, or otherwise embedded into or upon a removable oral appliance or other oral device to form a two-way communication assembly. The device contains a motion sensor to detect external forces imposed on the user such as an explosion, for example. The information is stored for medical treatment, among others. In another embodiment, the device provides an electronic and transducer device that can be attached, adhered, or otherwise embedded into or upon a removable oral appliance or other oral device to form a medical tag containing patient identifiable information. Such an oral appliance may be a custom-made device fabricated from a thermal forming process utilizing a replicate model of a dental structure obtained by conventional dental impression methods. The electronic and transducer assembly may receive incoming sounds either directly or through a receiver to process and amplify the signals and transmit the processed sounds via a vibrating transducer element coupled to a tooth or other bone structure, such as the maxillary, mandibular, or palatine bone structure.

24 Claims, 24 Drawing Sheets

U.S. PATENT DOCUMENTS

| | | |
|---|---|---|
| 4,150,262 A | 4/1979 | Ono |
| 4,498,461 A | 2/1985 | Hakansson |
| 4,591,668 A | 5/1986 | Iwata |
| 4,612,915 A | 9/1986 | Hough et al. |
| 4,642,769 A | 2/1987 | Petrofsky |
| 4,738,268 A | 4/1988 | Kipnis |
| 4,817,044 A | 3/1989 | Ogren |
| 4,832,033 A | 5/1989 | Maher et al. |
| 4,920,984 A | 5/1990 | Furumichi et al. |
| 4,982,434 A | 1/1991 | Lenhardt et al. |
| 5,012,520 A | 4/1991 | Steeger |
| 5,033,999 A | 7/1991 | Mersky |
| 5,047,994 A | 9/1991 | Lenhardt et al. |
| 5,060,526 A | 10/1991 | Barth et al. |
| 5,082,007 A | 1/1992 | Adell |
| 5,233,987 A | 8/1993 | Fabian et al. |
| 5,323,468 A | 6/1994 | Bottesch |
| 5,325,436 A | 6/1994 | Soli et al. |
| 5,372,142 A | 12/1994 | Madsen et al. |
| 5,402,496 A | 3/1995 | Soli et al. |
| 5,403,262 A | 4/1995 | Gooch |
| 5,447,489 A | 9/1995 | Issalene et al. |
| 5,455,842 A | 10/1995 | Merskey et al. |
| 5,460,593 A | 10/1995 | Mersky et al. |
| 5,546,459 A | 8/1996 | Sih et al. |
| 5,558,618 A | 9/1996 | Maniglia |
| 5,565,759 A | 10/1996 | Dunstan |
| 5,616,027 A | 4/1997 | Jacobs et al. |
| 5,624,376 A | 4/1997 | Ball et al. |
| 5,661,813 A | 8/1997 | Shimauchi et al. |
| 5,706,251 A | 1/1998 | May |
| 5,760,692 A | 6/1998 | Block |
| 5,800,336 A | 9/1998 | Ball et al. |
| 5,812,496 A | 9/1998 | Peck |
| 5,828,765 A | 10/1998 | Gable |
| 5,902,167 A | 5/1999 | Filo et al. |
| 5,914,701 A | 6/1999 | Gersheneld et al. |
| 5,961,443 A | 10/1999 | Rastatter et al. |
| 5,984,681 A | 11/1999 | Huang |
| 6,029,558 A | 2/2000 | Stevens et al. |
| 6,047,074 A | 4/2000 | Zoels et al. |
| 6,068,590 A | 5/2000 | Brisken |
| 6,072,884 A | 6/2000 | Kates |
| 6,072,885 A | 6/2000 | Stockham, Jr. et al. |
| 6,075,557 A | 6/2000 | Holliman et al. |
| 6,115,477 A | 9/2000 | Filo et al. |
| 6,118,882 A | 9/2000 | Haynes |
| 6,171,229 B1 | 1/2001 | Kroll et al. |
| 6,223,018 B1 | 4/2001 | Fukumoto et al. |
| 6,239,705 B1 | 5/2001 | Glen |
| 6,333,269 B2 | 12/2001 | Naito et al. |
| 6,377,693 B1 | 4/2002 | Lippa et al. |
| 6,394,969 B1 | 5/2002 | Lenhardt |
| 6,504,942 B1 | 1/2003 | Hong et al. |
| 6,538,558 B2 | 3/2003 | Sakazume et al. |
| 6,585,637 B2 | 7/2003 | Brillhart et al. |
| 6,631,197 B1 | 10/2003 | Taenzer |
| 6,633,747 B1 | 10/2003 | Reiss |
| 6,682,472 B1 | 1/2004 | Davis |
| 6,754,472 B1 | 6/2004 | Williams et al. |
| 6,778,674 B1 | 8/2004 | Panasik et al. |
| 6,826,284 B1 | 11/2004 | Benesty et al. |
| 6,885,753 B2 | 4/2005 | Bank |
| 6,917,688 B2 | 7/2005 | Yu et al. |
| 6,941,952 B1 | 9/2005 | Rush, III |
| 6,954,668 B1 | 10/2005 | Cuozzo |
| 6,985,599 B2 | 1/2006 | Asnes |
| 7,003,099 B1 | 2/2006 | Zhang et al. |
| 7,033,313 B2 | 4/2006 | Lupin et al. |
| 7,035,415 B2 | 4/2006 | Belt et al. |
| 7,074,222 B2 | 7/2006 | Westerkull |
| 7,076,077 B2 | 7/2006 | Atsumi et al. |
| 7,099,822 B2 | 8/2006 | Zangi |
| 7,162,420 B2 | 1/2007 | Zangi et al. |
| 7,171,003 B1 | 1/2007 | Venkatesh et al. |
| 7,171,008 B2 | 1/2007 | Elko |
| 7,174,022 B1 | 2/2007 | Zhang et al. |
| 7,206,423 B1 | 4/2007 | Feng et al. |
| 7,246,058 B2 | 7/2007 | Burnett |
| 7,258,533 B2 | 8/2007 | Tanner et al. |
| 7,269,266 B2 | 9/2007 | Anjanappa et al. |
| 7,271,569 B2 | 9/2007 | Oglesbee |
| 7,310,427 B2 | 12/2007 | Retchin et al. |
| 7,329,226 B1 | 2/2008 | Ni et al. |
| 7,331,349 B2 | 2/2008 | Brady et al. |
| 7,333,624 B2 | 2/2008 | Husung |
| 7,361,216 B2 | 4/2008 | Kangas et al. |
| 7,409,070 B2 | 8/2008 | Pitulia |
| 7,486,798 B2 | 2/2009 | Anjanappa et al. |
| 7,520,851 B2 | 4/2009 | Davis et al. |
| 7,522,738 B2 | 4/2009 | Miller, III |
| 7,522,740 B2 | 4/2009 | Julstrom et al. |
| 7,844,064 B2 * | 11/2010 | Abolfathi et al. ............ 381/326 |
| 2001/0003788 A1 | 6/2001 | Ball et al. |
| 2001/0051776 A1 | 12/2001 | Lenhardt |
| 2002/0026091 A1 | 2/2002 | Leysieffer |
| 2002/0071581 A1 | 6/2002 | Leysieffer et al. |
| 2002/0077831 A1 | 6/2002 | Numa |
| 2002/0122563 A1 | 9/2002 | Schumaier |
| 2002/0173697 A1 | 11/2002 | Lenhardt |
| 2003/0059078 A1 | 3/2003 | Downs et al. |
| 2003/0091200 A1 | 5/2003 | Pompei |
| 2003/0212319 A1 | 11/2003 | Magill |
| 2004/0057591 A1 | 3/2004 | Beck et al. |
| 2004/0131200 A1 | 7/2004 | Davis |
| 2004/0141624 A1 | 7/2004 | Davis et al. |
| 2004/0202339 A1 | 10/2004 | O'Brien, Jr. et al. |
| 2004/0202344 A1 | 10/2004 | Anjanappa et al. |
| 2004/0243481 A1 | 12/2004 | Bradbury et al. |
| 2004/0247143 A1 | 12/2004 | Lantrua et al. |
| 2005/0037312 A1 | 2/2005 | Uchida |
| 2005/0067816 A1 | 3/2005 | Buckman |
| 2005/0070782 A1 | 3/2005 | Brodkin |
| 2005/0129257 A1 | 6/2005 | Tamura |
| 2005/0196008 A1 | 9/2005 | Anjanappa et al. |
| 2005/0241646 A1 | 11/2005 | Sotos et al. |
| 2006/0008106 A1 | 1/2006 | Harper |
| 2006/0025648 A1 | 2/2006 | Lupin et al. |
| 2006/0064037 A1 | 3/2006 | Shalon et al. |
| 2006/0167335 A1 | 7/2006 | Park et al. |
| 2006/0270467 A1 | 11/2006 | Song et al. |
| 2006/0275739 A1 | 12/2006 | Ray |
| 2007/0010704 A1 | 1/2007 | Pitulia |
| 2007/0036370 A1 | 2/2007 | Granovetter et al. |
| 2007/0041595 A1 | 2/2007 | Carazo et al. |
| 2007/0142072 A1 | 6/2007 | Lassally |
| 2007/0230713 A1 | 10/2007 | Davis |
| 2007/0242835 A1 | 10/2007 | Davis |
| 2007/0265533 A1 | 11/2007 | Tran |
| 2007/0276270 A1 | 11/2007 | Tran |
| 2007/0280491 A1 | 12/2007 | Abolfathi |
| 2007/0280492 A1 | 12/2007 | Abolfathi |
| 2007/0280493 A1 | 12/2007 | Abolfathi |
| 2007/0280495 A1 | 12/2007 | Abolfathi |
| 2007/0286440 A1 | 12/2007 | Abolfathi et al. |
| 2007/0291972 A1 | 12/2007 | Abolfathi et al. |
| 2008/0019542 A1 | 1/2008 | Menzel et al. |
| 2008/0019557 A1 | 1/2008 | Bevirt et al. |
| 2008/0021327 A1 | 1/2008 | El-Bialy et al. |
| 2008/0064993 A1 | 3/2008 | Abolfathi et al. |
| 2008/0070181 A1 | 3/2008 | Abolfathi et al. |
| 2008/0146890 A1 * | 6/2008 | LeBoeuf et al. ............ 600/300 |
| 2008/0304677 A1 | 12/2008 | Abolfathi et al. |
| 2009/0028352 A1 | 1/2009 | Petroff |
| 2009/0052698 A1 | 2/2009 | Rader et al. |
| 2009/0088598 A1 | 4/2009 | Abolfathi |
| 2009/0097684 A1 | 4/2009 | Abolfathi et al. |
| 2009/0097685 A1 | 4/2009 | Menzel et al. |
| 2009/0099408 A1 | 4/2009 | Abolfathi et al. |
| 2009/0105523 A1 | 4/2009 | Kassayan et al. |
| 2009/0147976 A1 | 6/2009 | Abolfathi |
| 2009/0149722 A1 | 6/2009 | Abolfathi et al. |
| 2009/0180652 A1 | 7/2009 | Davis et al. |

FOREIGN PATENT DOCUMENTS

| | | |
|---|---|---|
| EP | 0741940 A1 | 11/1996 |
| EP | 0824889 A1 | 2/1998 |

| | | | |
|---|---|---|---|
| EP | 1299052 A1 | 2/2002 | |
| EP | 1633284 A1 | 12/2004 | |
| EP | 1691686 A1 | 8/2006 | |
| EP | 1718255 A1 | 11/2006 | |
| EP | 1783919 A1 | 5/2007 | |
| JP | 2007028248 A2 | 2/2007 | |
| JP | 2007028610 A2 | 2/2007 | |
| JP | 2007044284 A2 | 2/2007 | |
| JP | 2007049599 A2 | 2/2007 | |
| JP | 2007049658 A2 | 2/2007 | |
| WO | WO 83/02047 | 6/1983 | |
| WO | WO 91/02678 | 3/1991 | |
| WO | WO 95/19678 | 7/1995 | |
| WO | WO 96/21335 | 7/1996 | |
| WO | WO 02/09622 | 2/2002 | |
| WO | WO 2004/045242 | 5/2004 | |
| WO | WO 2004/105650 | 12/2004 | |
| WO | WO 2005/000391 | 1/2005 | |
| WO | WO 2005/037153 | 4/2005 | |
| WO | WO 2005/053533 | 6/2005 | |
| WO | WO 2006/088410 | 8/2006 | |
| WO | WO 2006/130909 | 12/2006 | |
| WO | WO 2007/043055 | 4/2007 | |
| WO | WO 2007/052251 | 5/2007 | |
| WO | WO 2007/059185 | 5/2007 | |
| WO | WO 2007/140367 | 12/2007 | |
| WO | WO 2007/140368 | 12/2007 | |
| WO | WO 2007/140373 | 12/2007 | |
| WO | WO 2007/143453 | 12/2007 | |
| WO | WO 2008/024794 | 2/2008 | |
| WO | WO 2008/030725 | 3/2008 | |
| WO | WO 2009/014812 | 1/2009 | |
| WO | WO 2009/025917 | 2/2009 | |
| WO | WO 2009/066296 | 5/2009 | |

OTHER PUBLICATIONS

"Special Forces Smart Noise Cancellation Ear Buds with Built-In GPS," http://www.gizmag.com/special-forces-smart-noise-cancellation-ear-buds-with-built-in-gps/9428/, 2 pages, 2008.

Altmann, et al. Foresighting the new technology waves—Exper Group. In: State of the Art Reviews and Related Papers—Center on Nanotechnology and Society. 2004 Conference. Published Jun. 14, 2004. p. 1-291. Available at http://www.nano-and-society.org.

Berard, G., "Hearing Equals Behavior" [summary], 1993, http://www.bixby.org/faq/tinnitus/treatment.html.

Dental Cements—Premarket Notification, U.S. Department of Health and Human Services Food and Drug Administration Center for Devices and Radiological Health, pp. 1-10, Aug. 18, 1998.

Henry, et al. "Comparison of Custom Sounds for Achieving Tinnitus Relief," *J Am Acad Audiol*,15:585-598, 2004.

Jastreboff, Pawel, J., "Phantom auditory perception (tinnitus): mechanisms of generation and perception," *Neuroscience Research*, 221-254, 1990, Elsevier Scientific Publishers Ireland, Ltd.

Robb, "Tinnitus Device Directory Part I," *Tinnitus Today*, p. 22, Jun. 2003.

Song, S. et al., "A 0.2-mW 2-Mb/s Digital Transceiver Based on Wideband Signaling for Human Body Communications," *IEEE J Solid-State Cir*, 42(9), 2021-2033, Sep. 2007.

Stuart, A., et al., "Investigations of the Impact of Altered Auditory Feedback In-The-Ear Devices on the Speech of People Who Stutter: Initial Fitting and 4-Month Follow-Up," *Int J Lang Commun Disord*, 39(1), Jan. 2004, [abstract only].

U.S. Appl. No. 11/672,239, filed Feb. 7, 2007 in the name of Abolfathi, Non-final Office Action mailed Jun. 18, 2009.

U.S. Appl. No. 11/672,239, filed Feb. 7, 2007 in the name of Abolfathi, Non-final Office Action mailed Nov. 13, 2008.

U.S. Appl. No. 11/672,250, filed Feb. 7, 2007 in the name of Abolfathi, Non-final Office Action mailed Apr. 21, 2009.

U.S. Appl. No. 11/672,250, filed Feb. 7, 2007 in the name of Abolfathi, Non-final Office Action mailed Aug. 8, 2008.

U.S. Appl. No. 11/672,264, filed Feb. 7, 2007 in the name of Abolfathi, Non-Final Rejection mailed Apr. 28, 2009.

U.S. Appl. No. 11/672,264, filed Feb. 7, 2007 in the name of Abolfathi, Non-Final Rejection mailed Aug. 6, 2008.

U.S. Appl. No. 11/672,271, filed Feb. 7, 2007 in the name of Abolfathi, Final Office Action mailed May 18, 2009.

U.S. Appl. No. 11/672,271, filed Feb. 7, 2007 in the name of Abolfathi, Non-final Office Action mailed Aug. 20, 2008.

U.S. Appl. No. 11/741,648, filed Apr. 27, 2007 in the name of Menzel et al., Final Office Action mailed May 18, 2009.

U.S. Appl. No. 11/741,648, filed Apr. 27, 2007 in the name of Menzel et al., Non-final Office Action mailed Sep. 4, 2008.

U.S. Appl. No. 11/754,823, filed May 29, 2007 in the name of Abolfathi et al., Final Office Action mailed May 12, 2009.

U.S. Appl. No. 11/754,823, filed May 29, 2007 in the name of Abolfathi et al., Non-final Office Action mailed Aug. 14, 2008.

U.S. Appl. No. 11/754,833, filed May 29, 2007 in the name of Abolfathi et al., Final Office Action mailed May 14, 2009.

U.S. Appl. No. 11/754,833, filed May 29, 2007 in the name of Abolfathi et al., Non-final Office Action mailed Aug. 6, 2008.

U.S. Appl. No. 11/866,345, filed May 29, 2007 in the name of Abolfathi et al., Final Office Action mailed Apr. 15, 2009.

U.S. Appl. No. 11/866,345, filed May 29, 2007 in the name of Abolfathi et al., Non-final Office Action mailed Mar. 19, 2008.

Wen, Y. et al, "Online Prediction of Battery Lifetime for Embedded and Mobile Devices," Special Issue on Embedded Systems: Springer-Verlag Heidelberg Lecture Notes in Computer Science, V3164/2004, 15 pages, Dec. 2004.

* cited by examiner

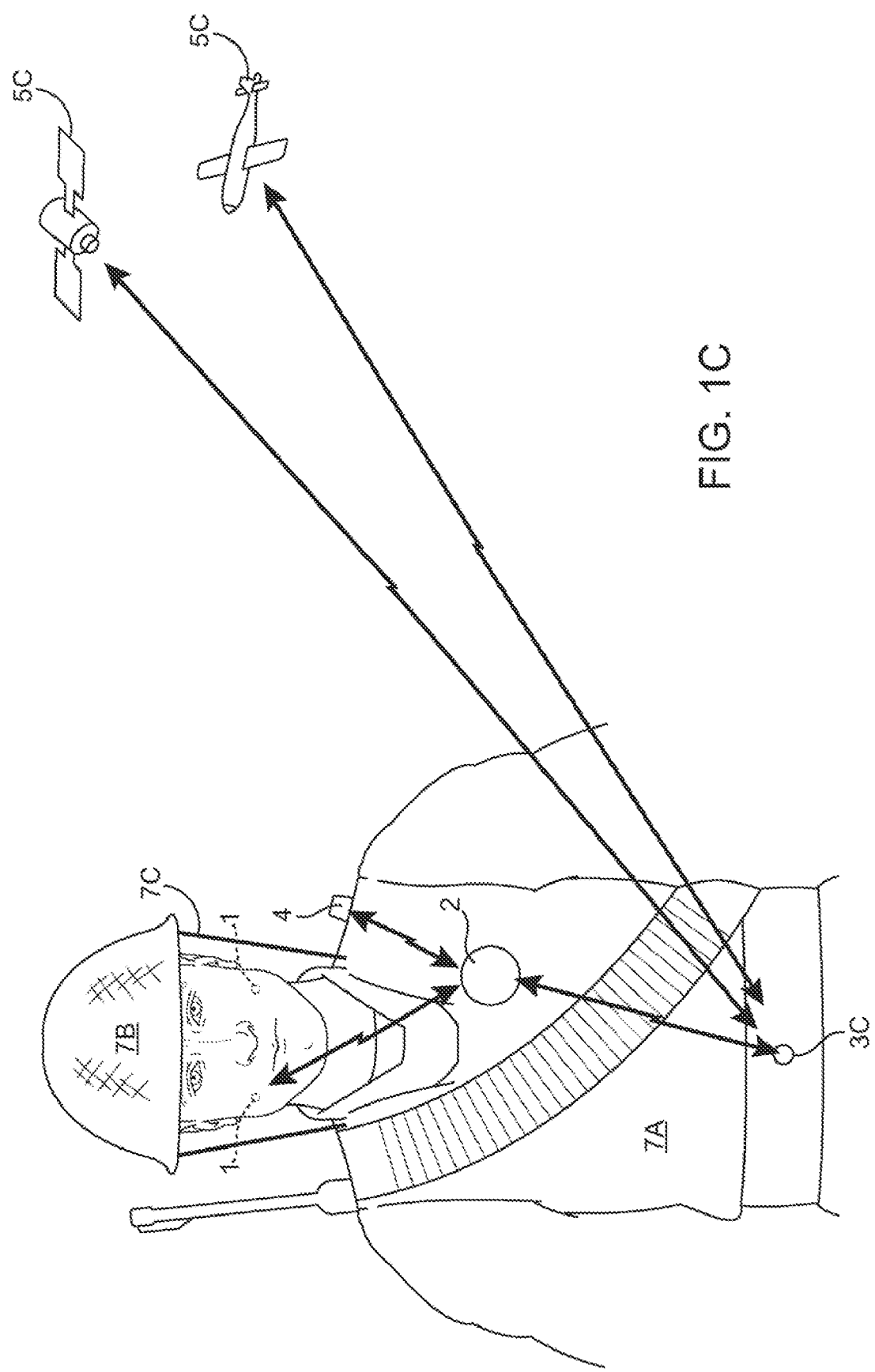

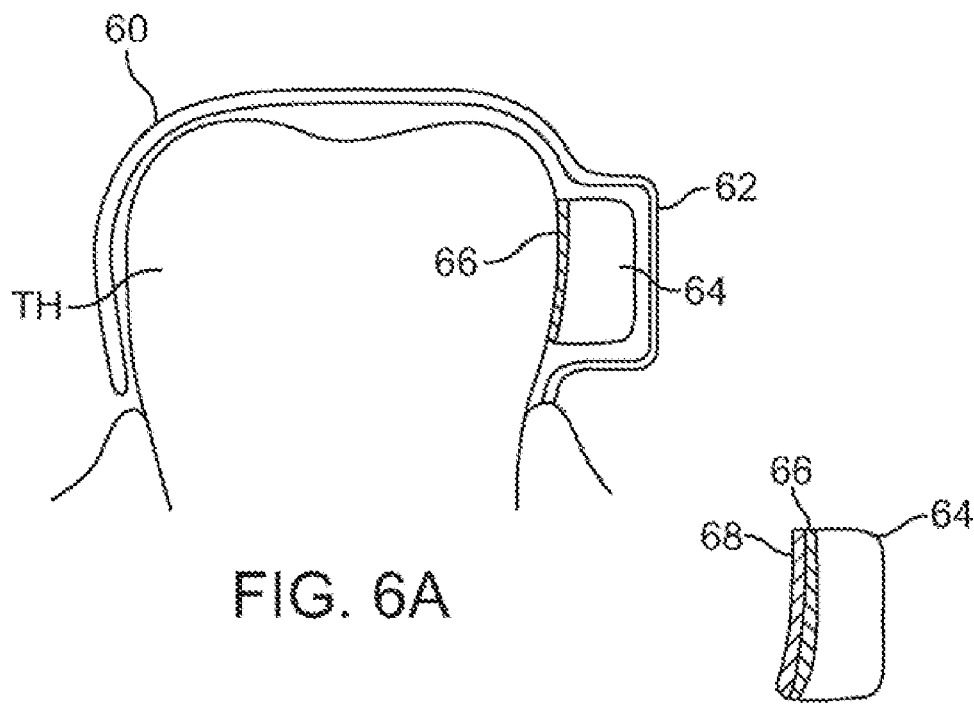
FIG. 6A
FIG. 6B
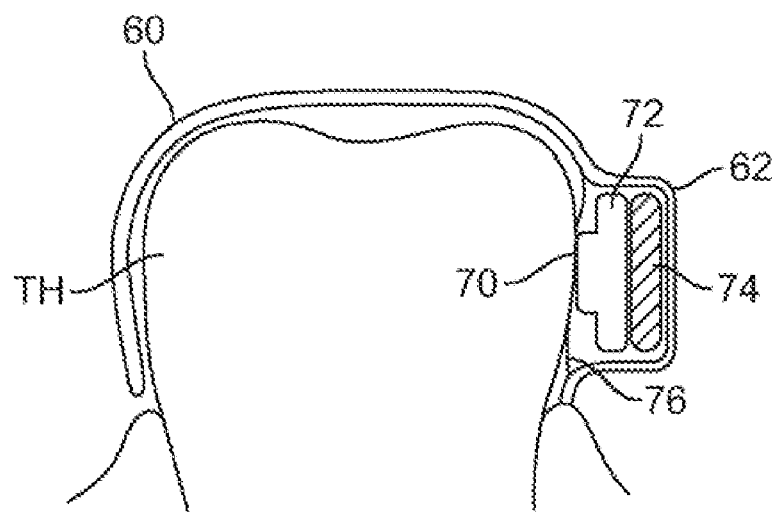
FIG. 7

SYSTEMS AND METHODS TO PROVIDE COMMUNICATION AND MONITORING OF USER STATUS

BACKGROUND

Millions of living Americans are serving, or have served, the nation in the armed services. Indeed, so many Americans have passed through military service that the Department of Defense (DoD) and individual branches of the armed forces has developed more than 60 separate clinical information systems since 1980 in an effort to keep track. These 60 disparate systems, while useful, resulted in an even greater diffusion of medical information, which became more difficult to access with each passing year. Therefore, the DoD was faced with the need for a "system of systems"—a comprehensive methodology that could meet the needs of the military not only in a hospital setting, but also in battlefield conditions. The solution was CHCS II-T. At full deployment, CHCS II-T will allow a physician, nurse practitioner or any other provider to get a patient's complete medical information right at the point of service, facilitating the delivery of care to active duty personnel, retirees and beneficiaries. CHCS II-T will ultimately be deployed on a mobile platform so frontline medical personnel can use the technology even under battlefield conditions.

Information technology initiatives, including CHCS II-T and the Preventive Health Care Application, are moving toward a complete computerized patient record that will capture and retain all health care information, improve the delivery of preventive services and health care, and enhance our understanding of the health status and needs of service members and their families. For the deployed military member, these systems will be able to share information with the PIC technology. The PIC is a wearable electronic tag that stores an individual's medical status and history, vaccination records and other essential information that will interface with CHCS II-T and other existing medical tracking systems in use in theater of operation. The PIC will be carried by Service members during deployment and updated by medical personnel using portable computers whenever the Service member is examined or treated. PIC information will be transmitted to consolidated databases to ensure that medical information is not lost if the PIC is lost or damaged.

The use of PIC tags, cards, armbands, and other information sources provides notice of unique medical conditions. In each instance, however, the individual must make the effort to maintain this information in a pocket or on his person. U.S. Pat. No. 4,557,693 discloses a device and method for applying and retaining a data carrier to a tooth surface of an individual. The data carrier has a thin sheet of material having a data format unique to the individual. This data carrier is attached to the surface of the individual's tooth and is adapted for detection by a reader which can be operated by a third person. The system further comprises a central data bank which becomes a verification source for identifying information carried at the individual's tooth surface.

In a parallel trend, certain high level members of the government, police, and military members engage in high risk jobs and need protection from gunshots and explosions. Conventional approaches include bullet-proof glass, concrete and steel building structures, armored cars, bullet-proof jackets, and others. The particular avenue taken depends on whether the person is stationary, located in a vehicle, located within a building, or is required to maintain mobility outside the confines of any specific stationary structure. U.S. Pat. No. 6,029,558 discloses the use of an air bag which is rapidly inflated and interposed between the projectile or concussive force and the person to be protected so as to either deflect the projectile or reduce the effects of the concussive force.

SUMMARY

Methods and apparatus that support communications and/or medical information monitoring for soldiers are disclosed.

In one aspect, a bone conduction communication apparatus includes a housing having a shape which is conformable to at least a portion of at least one tooth of a user; a motion sensor to detect a force imposed on the user; an actuatable transducer disposed within or upon the housing and in vibratory communication with a surface of the at least one tooth; and a wireless satellite transceiver coupled to the motion sensor to communicate the force and coupled to the transducer to provide received sound to the user and to support global communication for the user.

In another aspect, an electronic and transducer device can be attached, adhered, or otherwise embedded into or upon a removable oral appliance or other oral device to form a two-way communication assembly. The device contains a motion sensor to detect external forces imposed on the user such as an explosion, for example. The information is stored for medical treatment, among others. In another embodiment, the device provides an electronic and transducer device that can be attached, adhered, or otherwise embedded into or upon a removable oral appliance or other oral device to form a medical tag containing patient identifiable information. Such an oral appliance may be a custom-made device fabricated from a thermal forming process utilizing a replicate model of a dental structure obtained by conventional dental impression methods. The electronic and transducer assembly may receive incoming sounds either directly or through a receiver to process and amplify the signals and transmit the processed sounds via a vibrating transducer element coupled to a tooth or other bone structure, such as the maxillary, mandibular, or palatine bone structure.

The system reduces paperwork, allows for the collection of more complete patient information, eliminates redundant data entry, increases responsiveness to medical situations and enables healthcare providers to make certain all patient episodes are captured and recorded no matter the environment. Most importantly; the system provides a standard of care to our soldiers by providing access to previously unavailable information. The system is a multi-purpose medical platform that is rugged, wireless and secure. The system provides commanders with real time visibility of their readiness status and provides support for medical command and control, telemedicine and medical informatics applications across the continuum of the entire spectrum of military medical operations but especially for the first responder and far forward medical facilities. With soldiers deployed in many different parts of the world, the system allows medical professionals to capture patient episodes anywhere, anytime, and ensure complete patient information is recorded and transferred to the soldier's medical record at home.

Certain embodiments of the system automatically inflates Kevlar coated jackets and helmets to protect the user from the forces of blasts or explosions. These embodiments receive the output of the motion sensors and detect the presence of blasts/explosions and cause the vests/helmets to become hardened to protect the wearer from the blasts/explosions. The system can provide an automated introduction of a protective, inflatable shield between the concussive force of a bomb blast or the impact energy of a projectile, and the body of the person at which it is directed.

The system is uniquely tailored to the individual and can contain tamper-proof electronics that disable the system if the system is removed from the authorized user and tampered with in order to be used by an unauthorized user. In this manner, the system is highly secured. Due to the security, the system can provide a dental identification means which is retained on the individual and thus is less subject to destruction, loss, forgetfulness, or any of the numerous other problems.

BRIEF DESCRIPTION OF THE DRAWINGS

FIG. 1C shows a third embodiment of an exemplary communication device and/or medical monitoring device.

FIG. 6A shows a partial cross-sectional view of an oral appliance placed upon a tooth with an electronics/transducer assembly adhered to the tooth surface via an adhesive.

FIG. 6B shows a partial cross-sectional view of a removable backing adhered onto an adhesive surface.

FIG. 7 shows a partial cross-sectional view of another variation of an oral appliance placed upon a tooth with an electronics/transducer assembly pressed against the tooth surface via an osmotic pouch.

DESCRIPTION

Figure 1A:
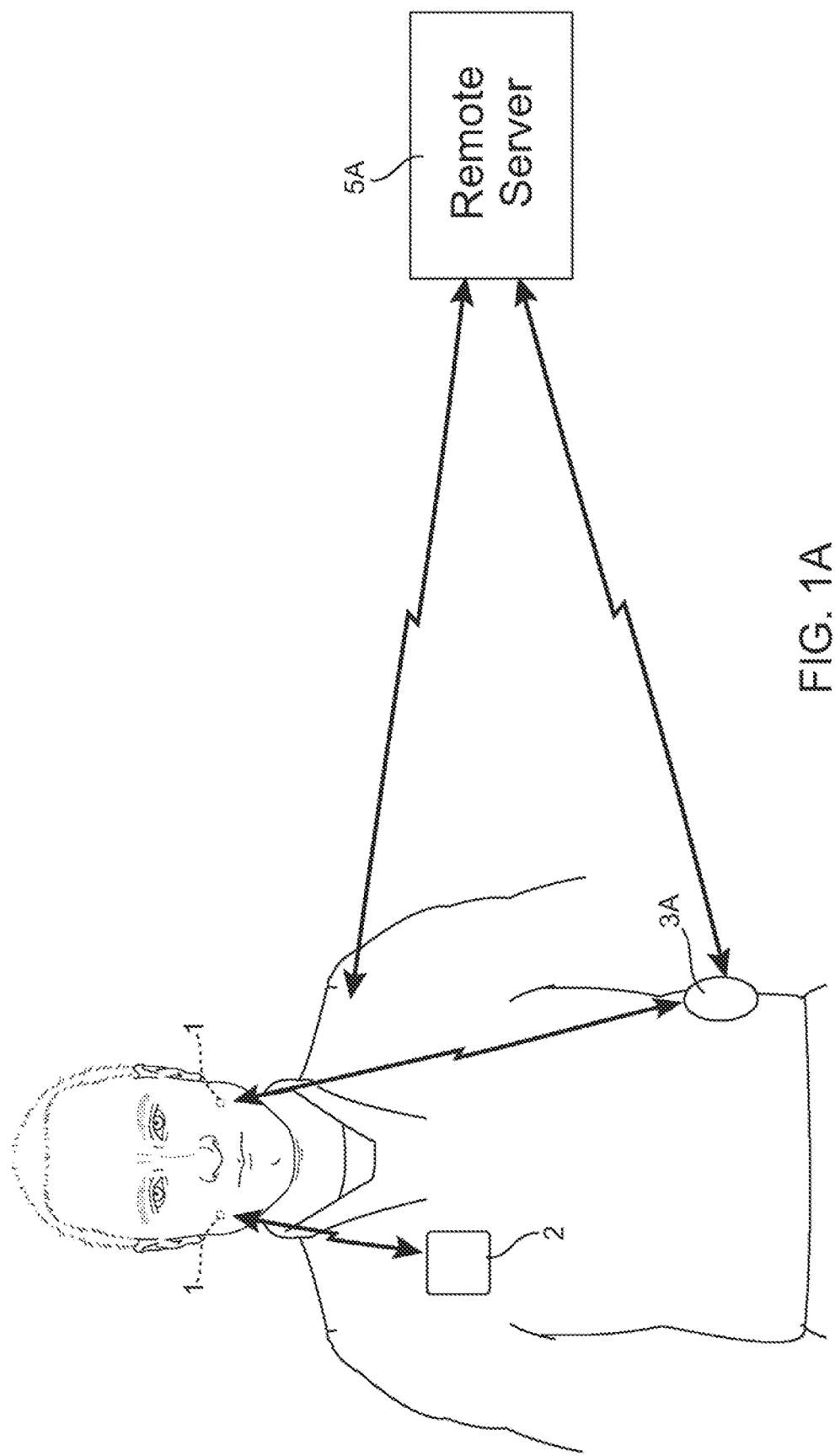
FIG. 1A shows a first embodiment of an exemplary communication device and/or medical monitoring device.

As shown in FIG. 1A, an exemplary two way communication device and/or monitoring device 1 is shown. In one embodiment, the device 1 provides an electronic and transducer device that can be attached, adhered, or otherwise embedded into or upon an intraoral appliance/device or a removable oral appliance/device to form a two-way communication assembly. The appliance or device 1 can be used by emergency personnel, medical personnel, soldiers, or any one working in a high noise environment, among others.

In the embodiment of FIG. 1A, the device 1 is mounted in the user's mouth. More details on the intraoral device 1 are discussed below. The device 1 can communicate with one or more body mounted sensors 2 through a short range personal area network (PAN). The device 1 can also communicate with an attention device 4 such as a flashing light, among others. In case of an emergency with poor visibility, the attention device 4 can be activated to identify the wearer so that assistance can be rendered quickly. The device 1, the sensor 2 and attention device 4 communicates with a long range transceiver 3A. In the embodiment of FIG. 1A, the system communicates through a remote server 5A over a long range wireless area network such as WiMAX.

In one embodiment, the device 1 provides an electronic and transducer device that can be attached, adhered, or otherwise embedded into or upon a removable oral appliance or other oral device to form a medical tag containing patient identifiable information. Such an oral appliance may be a custom-made device fabricated from a thermal forming process utilizing a replicate model of a dental structure obtained by conventional dental impression methods. The electronic and transducer assembly may receive incoming sounds either directly or through a receiver to process and amplify the signals and transmit the processed sounds via a vibrating transducer element coupled to a tooth or other bone structure, such as the maxillary, mandibular, or palatine bone structure.

Figure 1B:
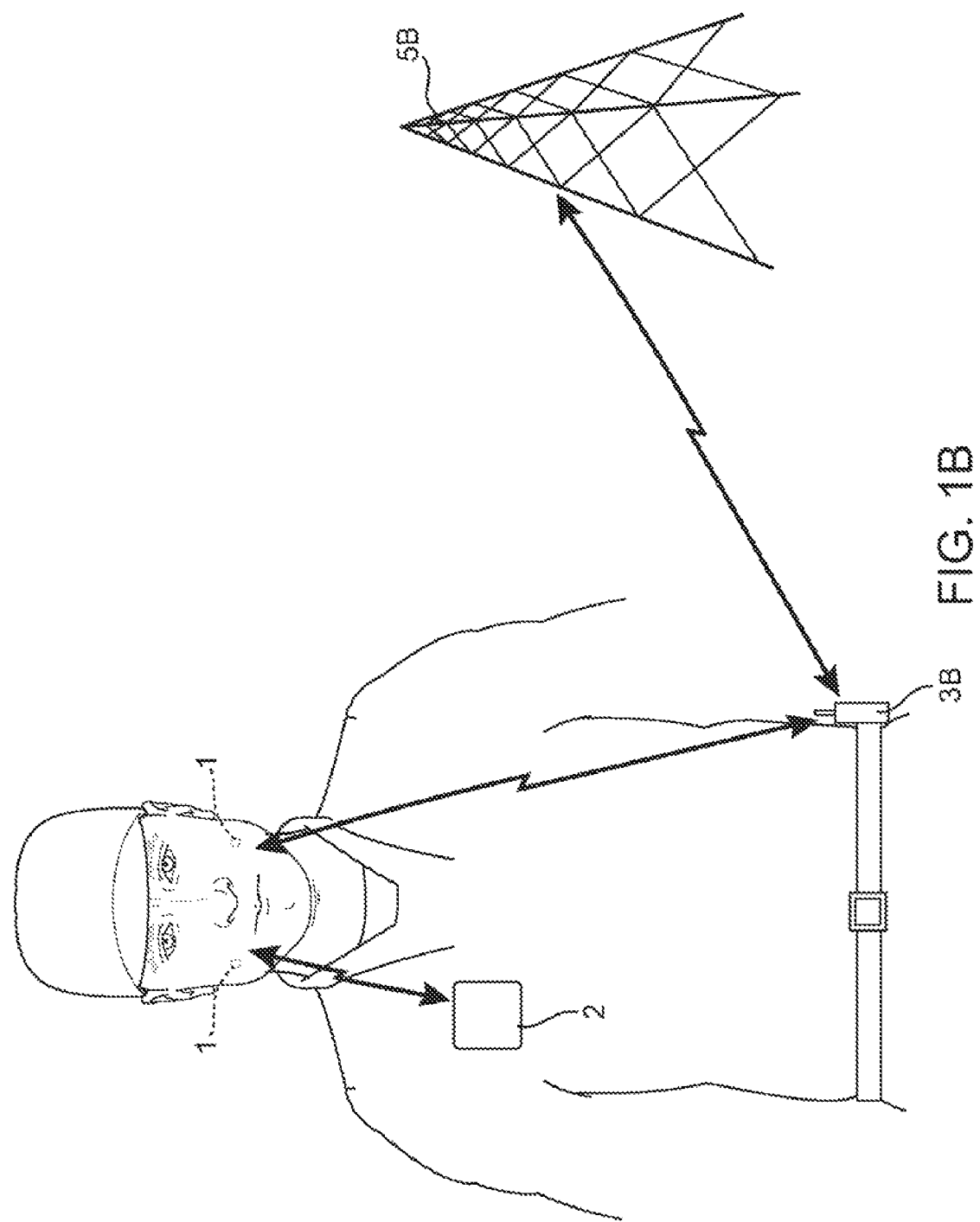
FIG. 1B shows a second embodiment of an exemplary communication device and/or medical monitoring device.

FIG. 1B shows an exemplary embodiment used in high noise industrial settings. In the embodiment of FIG. 1B, multiple sensors 2 and 2' can be used. Also, the transceiver 3B is a cellular transceiver that communicates with cellular towers 5B, among others.

In a military application as shown in FIG. 1C, the device 1 can include sensors that detect chemicals present in the soldier's saliva and provide medical information on the soldier. Additionally, in certain embodiments, the device 1 can also sense heart rate, EKG, and other bio-signals that can be picked up within the mouth. Additionally, the device 1 can communicate with the medical data collection module 2 that can collect heart rate, EKG, respiration rate, and other vital signs or medical information. The device 1 can communicate with the module 2 through various short range radios such as a Bluetooth radio, for example, or through body conduction transceivers, among others.

In another embodiment, the device 1 is custom-fit to the user and will not be usable by another individual if transplanted to another user such as through hostile action by an enemy or through an intentional action by the wearer. This will be done by the fact that it is custom-fit to the user. Further, in one embodiment, if the device is tampered with, anti-tampering circuitry in the device 1 will render the device non-functional.

The device 1 can also communicate with a long range transceiver such as a short-wave transceiver 3A, a cellular telephone transceiver 3B, or a satellite transceiver 3C. Such transceivers can be provided within the device 1, or alternatively, can be body worn. In the embodiment of FIG. 1C, the satellite transceiver 3C is positioned on a belt worn by the soldier. The satellite transceiver 3C communicates with the device 1 through the short range radio such as Bluetooth, for example.

The device 1 can contain a motion sensor such as an accelerometer. The motion sensor can store information on external forces that are imposed on the user such as the forces arising from a bomb blast. The accelerometer measures the total specific external force on the sensor. The accelerometer can be a micro electro-mechanical system (MEMS) device that includes a suspended cantilever beam or proof mass (also known as seismic mass) with deflection sensing and circuitry. Other methods of building MEMS based accelerometers are known.

In one embodiment, the accelerometer is a 3 axis accelerometer that can capture the blast vector including direction and magnitude of the force. The blast vector is stored in memory and can also be transmitted to a remote monitoring center. For example, the motion sensor output can be provided to the long range transceiver for remote monitoring of the well being of the user. If a blast is detected, medical assistance can be sent to save the user from harm. In another embodiment, historical blast vector information can be analyzed for injury trend analysis and subsequent treatment even if the soldier reports no immediate medical injury.

In another embodiment, the accelerometer output is used to activate a reactive personnel protection system which, upon detecting the presence of a destructive force or object, interposes a protective shield between personnel under attack and the force in an almost instantaneous fashion. To protect against a concussive blast triggered by a bomb explosion, the output of the accelerometer triggers a rapid inflation of a vest 7A with an air bag worn by the user. The air bag can be fabricated from Kevlar® or similar materials. The air bag is rapidly inflated and interposed between a projectile or a concussive force and the person to be protected so as to either deflect the projectile or reduce the effects of the concussive force.

In another embodiment, the airbag can have a linkage 7C to a helmet 7B and the linkage is automatically inflated when the accelerometer senses the destructive force or object. When inflated, the vest 7A, the linkage 7C and the helmet 7B is hardened to protect the user from neck injury and other bodily harm(s).

The accelerometer senses an explosion or a bullet by sensing rapid changes in acceleration and/or air pressure (e.g. the concussive wave front which accompanies an explosion). Other devices, such as magnetostrictive transducers, ultrasonic transducers, accelerometers, and other mechanical and/or electro-mechanical sensors can also be applied to sense the occurrence of a concussive explosion.

The forces of the concussive explosion and/or vital signs of the user can be automatically transmitted to a remote monitoring center that can dispatch help if required. An exemplary process to collect medical information from the patient and for supporting bone-conduction two way communication can be as follows:

Periodically collect medical information

Check to see if the soldier is using the long range transceiver for talking

If long range transceiver is not used for talking, upload medical history of the soldier to a remote computer over the long range transceiver Remote computer detects if the medical data falls outside of an acceptable range that requires medical intervention If medical intervention is required, the remote computer alerts the soldier's commander for action to assist the soldier Self-help instructions can be sent through the satellite transceiver to the bone conduction communication device 1

In one embodiment, the medical data would include soldier identification, triage status, condition, and treatment. The data would be routed via the satellite transceiver to a Command Post where it is processed, stored, relayed to the Internet, and moved back to devices on the field. As a result, data on casualties would be accessible immediately for operational use by other soldiers, medics, responders, incident commanders and even receiving hospitals that can help the soldier. Real-time information regarding victims and their status is critical to the overall management of field medical care. Medical command can then coordinate timely information on the number of casualties and their needs with the known availability of resources, such as on-scene providers, ambulance locations, and area hospital capacities. Real-time information is also provided for determining the appropriate patient destination, depending on the type of injuries and the capabilities of the receiving facilities.

In another embodiment, the remote computer can support a BATTLEFIELD MEDICAL INFORMATION SYSTEMS TACTICAL-JOINT (BMIST-J) for enabling military providers to record, store, retrieve and transfer medical records to the DoD's Clinical Data Repository by synchronizing the received data. The system supports digital versions of the DD 1380 (field medical card) and SF 600 (chronological medical record of care). Diagnostic and treatment decision aids are provided by the system. The data captured by the device 1 is also Personal Information Carrier (PIC) compatible. The system provides a secure, legible, electronic records of battlefield treatments, contributes to a comprehensive, life-long medical history, and facilitates medical surveillance.

Figure 1D:
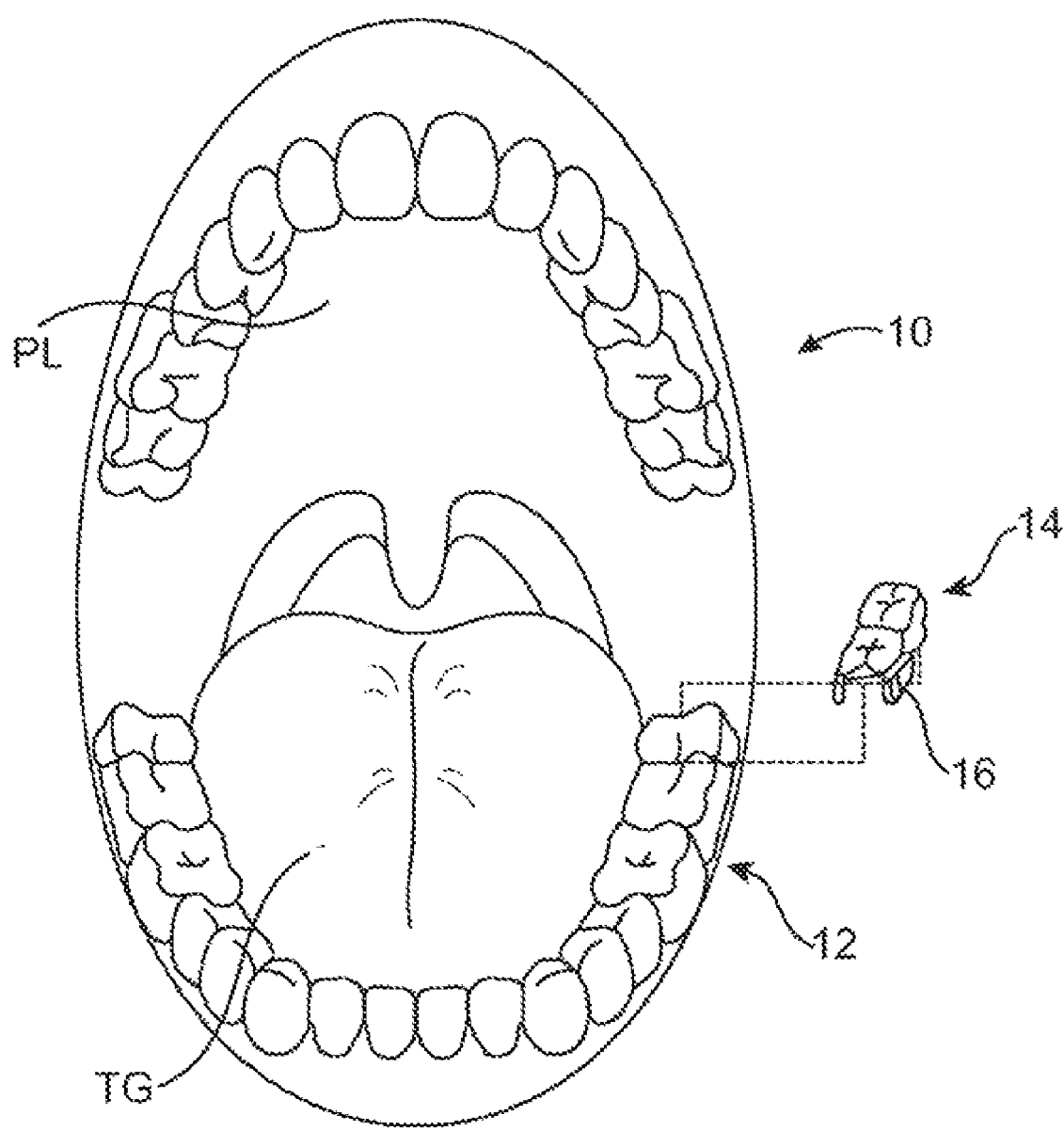
FIG. 1D illustrates the dentition of a patient's teeth and one variation of a two-way communication device which is removably placed upon or against the patient's tooth or teeth as a removable oral appliance.

Turning now to more details on the device 1, as shown in FIG. 1D, a patient's mouth and dentition 10 is illustrated showing one possible location for removably attaching two-way communication assembly 14 upon or against at least one tooth, such as a molar 12. The patient's tongue TG and palate PL are also illustrated for reference. An electronics and/or transducer assembly 16 may be attached, adhered, or otherwise embedded into or upon the assembly 14, as described below in further detail.

Figure 2A:
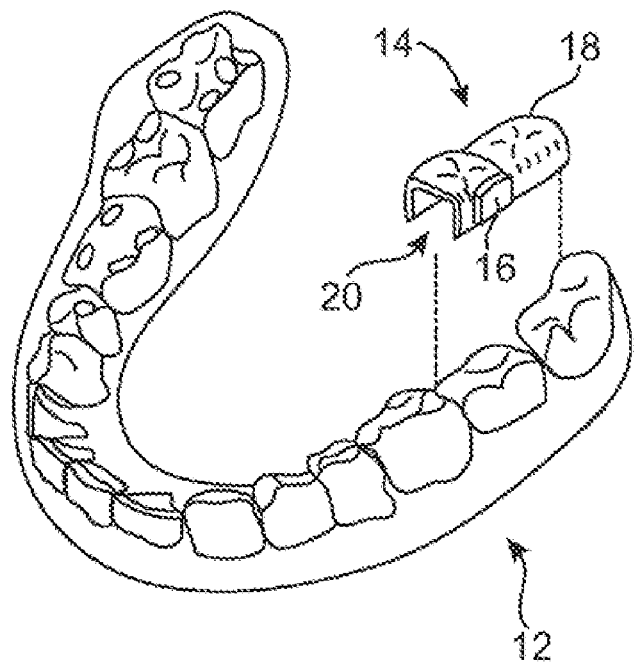
FIG. 2A illustrates a perspective view of the lower teeth showing one exemplary location for placement of the removable oral appliance two-way communication device.

FIG. 2A shows a perspective view of the patient's lower dentition illustrating the two-way communication assembly 14 comprising a removable oral appliance 18 and the electronics and/or transducer assembly 16 positioned along a side surface of the assembly 14. In this variation, oral appliance 18 may be fitted upon two molars 12 within tooth engaging channel 20 defined by oral appliance 18 for stability upon the patient's teeth, although in other variations, a single molar or tooth may be utilized. Alternatively, more than two molars may be utilized for the oral appliance 18 to be attached upon or over. Moreover, electronics and/or transducer assembly 16 is shown positioned upon a side surface of oral appliance 18 such that the assembly 16 is aligned along a buccal surface of the tooth 12; however, other surfaces such as the lingual surface of the tooth 12 and other positions may also be utilized. The figures are illustrative of variations and are not intended to be limiting; accordingly, other configurations and shapes for oral appliance 18 are intended to be included herein.

Figure 2B:
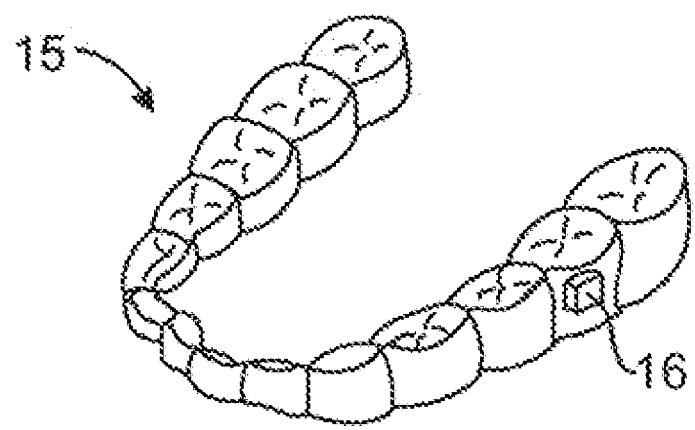
FIG. 2B illustrates another variation of the removable oral appliance in the form of an appliance which is placed over an entire row of teeth in the manner of a mouthguard.

FIG. 2B shows another variation of a removable oral appliance in the form of an appliance 15 which is placed over an entire row of teeth in the manner of a mouthguard. In this variation, appliance 15 may be configured to cover an entire bottom row of teeth or alternatively an entire upper row of teeth. In additional variations, rather than covering the entire rows of teeth, a majority of the row of teeth may be instead be covered by appliance 15. Assembly 16 may be positioned along one or more portions of the oral appliance 15.

Figure 2C:
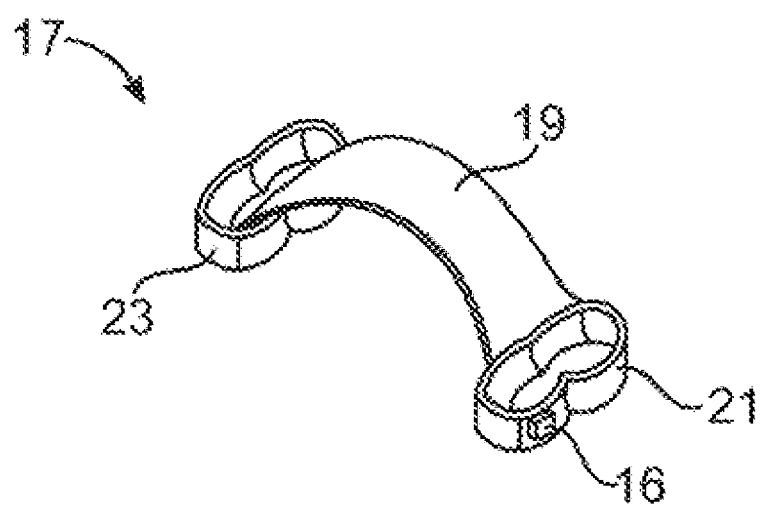
FIG. 2C illustrates another variation of the removable oral appliance which is supported by an arch.

FIG. 2C shows yet another variation of an oral appliance 17 having an arched configuration. In this appliance, one or more tooth retaining portions 21, 23, which in this variation may be placed along the upper row of teeth, may be supported by an arch 19 which may lie adjacent or along the palate of the user. As shown, electronics and/or transducer assembly 16 may be positioned along one or more portions of the tooth retaining portions 21, 23. Moreover, although the variation shown illustrates an arch 19 which may cover only a portion of the palate of the user, other variations may be configured to have an arch which covers the entire palate of the user.

Figure 2D:
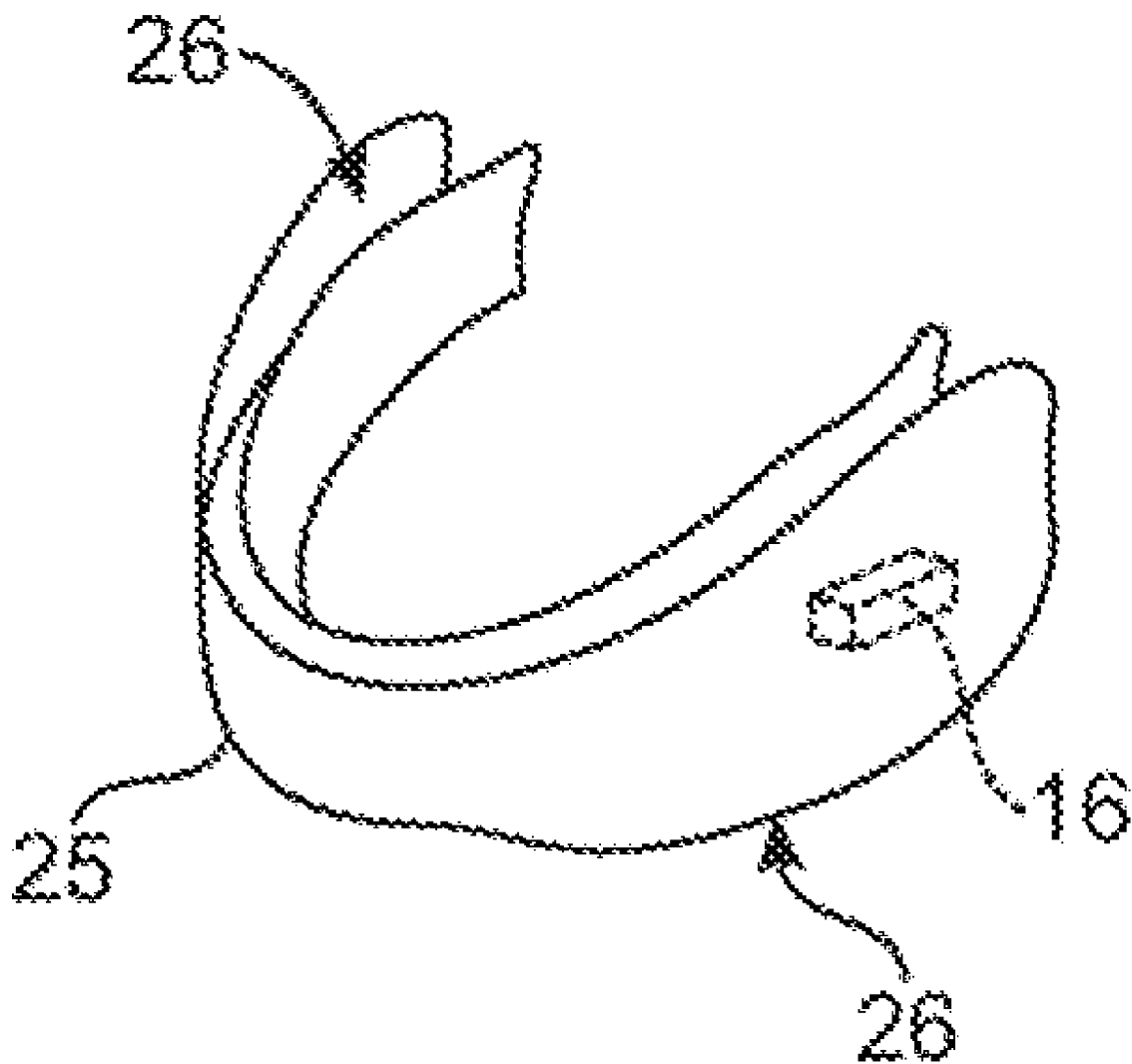
FIG. 2D illustrates another variation of an oral appliance configured as a mouthguard.

FIG. 2D illustrates yet another variation of an oral appliance in the form of a mouthguard or retainer 25 which may be inserted and removed easily from the user's mouth. Such a mouthguard or retainer 25 may be used in sports where conventional mouthguards are worn; however, mouthguard or retainer 25 having assembly 16 integrated therein may be utilized by persons, hearing impaired or otherwise, who may simply hold the mouthguard or retainer 25 via grooves or channels 26 between their teeth for receiving instructions remotely and communicating over a distance.

Generally, the volume of electronics and/or transducer assembly 16 may be minimized so as to be unobtrusive and as comfortable to the user when placed in the mouth. Although the size may be varied, a volume of assembly 16 may be less than 800 cubic millimeters. This volume is, of course, illustrative and not limiting as size and volume of assembly 16 and may be varied accordingly between different users.

Moreover, removable oral appliance 18 may be fabricated from various polymeric or a combination of polymeric and metallic materials using any number of methods, such as computer-aided machining processes using computer numerical control (CNC) systems or three-dimensional printing processes, e.g., stereolithography apparatus (SLA), selective laser sintering (SLS), and/or other similar processes utilizing three-dimensional geometry of the patient's dentition, which may be obtained via any number of techniques. Such techniques may include use of scanned dentition using intra-oral scanners such as laser, white light, ultrasound, mechanical three-dimensional touch scanners, magnetic resonance imaging (MRI), computed tomography (CT), other optical methods, etc.

In forming the removable oral appliance 18, the appliance 18 may be optionally formed such that it is molded to fit over the dentition and at least a portion of the adjacent gingival tissue to inhibit the entry of food, fluids, and other debris into the oral appliance 18 and between the transducer assembly and tooth surface. Moreover, the greater surface area of the oral appliance 18 may facilitate the placement and configuration of the assembly 16 onto the appliance 18.

Additionally, the removable oral appliance 18 may be optionally fabricated to have a shrinkage factor such that when placed onto the dentition, oral appliance 18 may be configured to securely grab onto the tooth or teeth as the appliance 18 may have a resulting size slightly smaller than the scanned tooth or teeth upon which the appliance 18 was formed. The fitting may result in a secure interference fit between the appliance 18 and underlying dentition.

Figure 3:
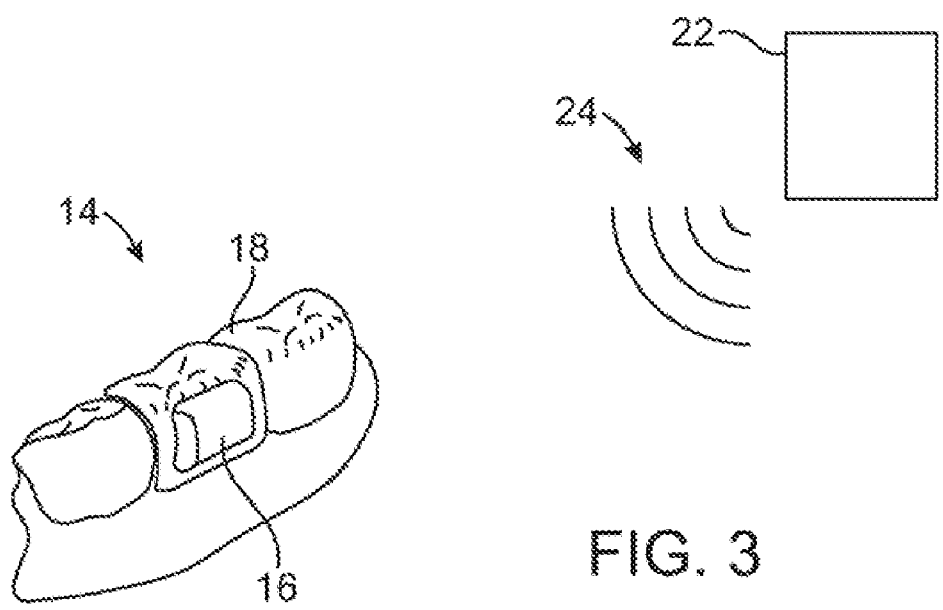
FIG. 3 illustrates a detail perspective view of the oral appliance positioned upon the patient's teeth utilizable in combination with a transmitting assembly external to the mouth and wearable by the patient in another variation of the device.

In one variation, with assembly 14 positioned upon the teeth, as shown in FIG. 3, an extra-buccal transmitter assembly 22 located outside the patient's mouth may be utilized to receive auditory signals for processing and transmission via a wireless signal 24 to the electronics and/or transducer assembly 16 positioned within the patient's mouth, which may then process and transmit the processed auditory signals via vibratory conductance to the underlying tooth and consequently to the patient's inner ear.

The transmitter assembly 22, as described in further detail below, may contain a microphone assembly as well as a transmitter assembly and may be configured in any number of shapes and forms worn by the user, such as a watch, necklace, lapel, phone, belt-mounted device, etc.

Figure 4:
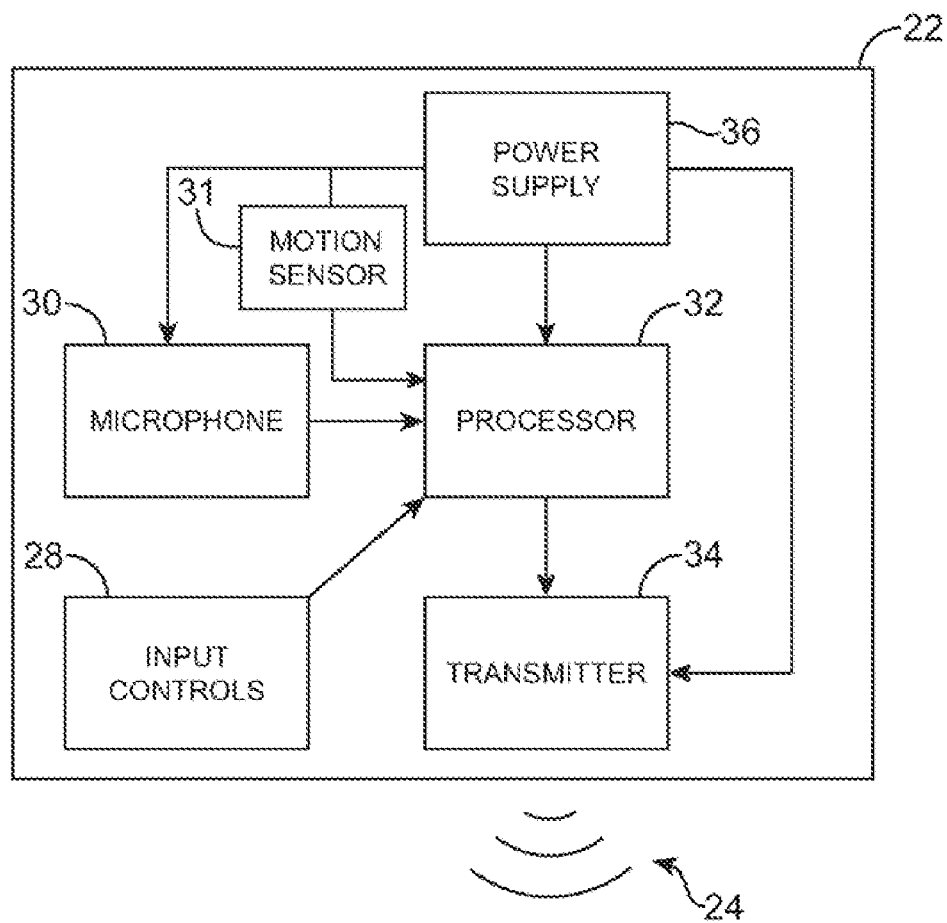
FIG. 4 shows an illustrative configuration of the individual components in a variation of the oral appliance device having an external transmitting assembly with a receiving and transducer assembly within the mouth.
Figure 4:
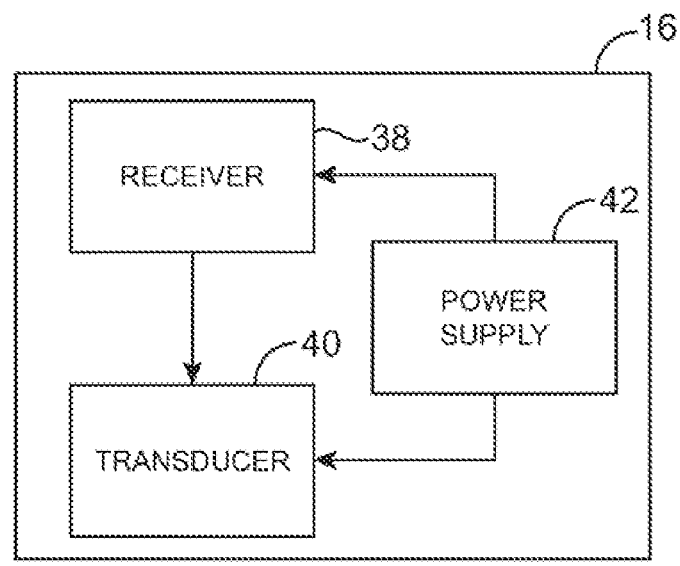

FIG. 4 illustrates a schematic representation of one variation of two-way communication assembly 14 utilizing an extra-buccal transmitter assembly 22, which may generally comprise microphone 30 for receiving sounds and which is electrically connected to processor 32 for processing the auditory signals. The assembly 14 includes motion sensor 31 whose output is connected to processor 32. Motion sensor 31 can be a three axis accelerometer, among others. For small size, the accelerometer can be a MEMS accelerometer. Processor 32 may be connected electrically to transmitter 34 for transmitting the processed signals to the electronics and/or transducer assembly 16 disposed upon or adjacent to the user's teeth. The microphone 30 and processor 32 may be configured to detect and process auditory signals in any practicable range, but may be configured in one variation to detect auditory signals ranging from, e.g., 250 Hertz to 20,000 Hertz.

With respect to microphone 30, a variety of various microphone systems may be utilized. For instance, microphone 30 may be a digital, analog, and/or directional type microphone. Such various types of microphones may be interchangeably configured to be utilized with the assembly, if so desired.

Power supply 36 may be connected to each of the components in transmitter assembly 22 to provide power thereto. The transmitter signals 24 may be in any wireless form utilizing, e.g., radio frequency, ultrasound, microwave, Blue Tooth® (BLUETOOTH SIG, INC., Bellevue, Wash.), etc. for transmission to assembly 16. Assembly 22 may also optionally include one or more input controls 28 that a user may manipulate to adjust various acoustic parameters of the electronics and/or transducer assembly 16, such as acoustic focusing, volume control, filtration, muting, frequency optimization, sound adjustments, and tone adjustments, etc.

The signals transmitted 24 by transmitter 34 may be received by electronics and/or transducer assembly 16 via receiver 38, which may be connected to an internal processor for additional processing of the received signals. The received signals may be communicated to transducer 40, which may vibrate correspondingly against a surface of the tooth to conduct the vibratory signals through the tooth and bone and subsequently to the middle ear to facilitate hearing of the user. Transducer 40 may be configured as any number of different vibratory mechanisms. For instance, in one variation, transducer 40 may be an electromagnetically actuated transducer. In other variations, transducer 40 may be in the form of a piezoelectric crystal having a range of vibratory frequencies, e.g., between 250 to 4000 Hz.

Power supply 42 may also be included with assembly 16 to provide power to the receiver, transducer, and/or processor, if also included. Although power supply 42 may be a simple battery, replaceable or permanent, other variations may include a power supply 42 which is charged by inductance via an external charger. Additionally, power supply 42 may alternatively be charged via direct coupling to an alternating current (AC) or direct current (DC) source. Other variations may include a power supply 42 which is charged via a mechanical mechanism, such as an internal pendulum or slidable electrical inductance charger as known in the art, which is actuated via, e.g., motions of the jaw and/or movement for translating the mechanical motion into stored electrical energy for charging power supply 42.

Figure 5:
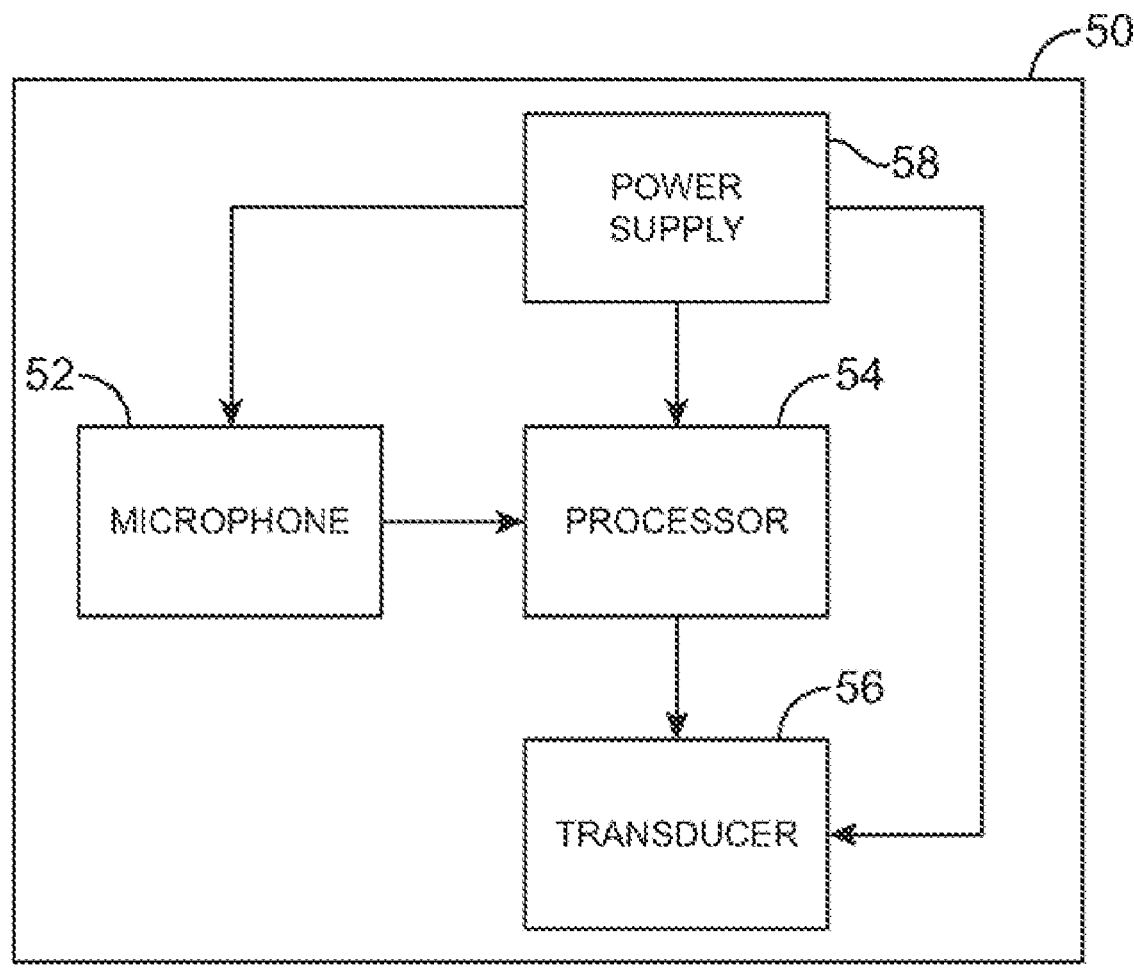
FIG. 5 shows an illustrative configuration of another variation of the device in which the entire assembly is contained by the oral appliance within the user's mouth.

In another variation of assembly 16, rather than utilizing an extra-buccal transmitter, two-way communication assembly 50 may be configured as an independent assembly contained entirely within the user's mouth, as shown in FIG. 5. Accordingly, assembly 50 may include an internal microphone 52 in communication with an on-board processor 54. Internal microphone 52 may comprise any number of different types of microphones, as described above. Processor 54 may be used to process any received auditory signals for filtering and/or amplifying the signals and transmitting them to transducer 56, which is in vibratory contact against the tooth surface. Power supply 58, as described above, may also be included within assembly 50 for providing power to each of the components of assembly 50 as necessary.

In order to transmit the vibrations corresponding to the received auditory signals efficiently and with minimal loss to the tooth or teeth, secure mechanical contact between the transducer and the tooth is ideally maintained to ensure efficient vibratory communication. Accordingly, any number of mechanisms may be utilized to maintain this vibratory communication.

In one variation as shown in FIG. 6A, a partial cross-sectional view of a removable oral appliance 60 is shown placed over or upon a tooth TH. Electronics and/or transducer housing 62 may be seen defined along oral appliance 60 such that housing 62 is aligned or positioned adjacent to a side surface, buccal and/or lingual surface, of the tooth TH. Housing 62 may provide protection to the electronics and/or transducer assembly from the environment of the mouth.

An electronics and/or transducer assembly 64 may be simply placed, embedded, or encapsulated within housing 62 for contacting the tooth surface. In this variation, assembly 64 may be adhered against the tooth surface via an adhesive surface or film 66 such that contact is maintained between the two. As shown in FIG. 6B, a removable backing 68 may be adhered onto adhesive surface 66 and removed prior to placement upon the tooth surface. In this manner, assembly 64 may be replaced upon the tooth as necessary with additional electronics and/or transducer assemblies.

Aside from an adhesive film 66, another alternative may utilize an expandable or swellable member to ensure a secure mechanical contact of the transducer against the tooth. As shown in FIG. 7, an osmotic patch or expandable hydrogel 74 may be placed between housing 62 and electronics and/or transducer assembly 72. After placement of oral appliance 60, hydrogel 74 may absorb some fluids, either from any surrounding fluid or from a fluid introduced into hydrogel 74, such that hydrogel 74 expands in size to force assembly 72 into contact against the tooth surface. Assembly 72 may be configured to define a contact surface 70 having a relatively smaller contact area to facilitate uniform contact of the surface 70 against the tooth. Such a contact surface 70 may be included in any of the variations described herein. Additionally, a thin encapsulating layer or surface 76 may be placed over housing 62 between contact surface 70 and the underlying tooth to prevent any debris or additional fluids from entering housing 62.

Figure 8:
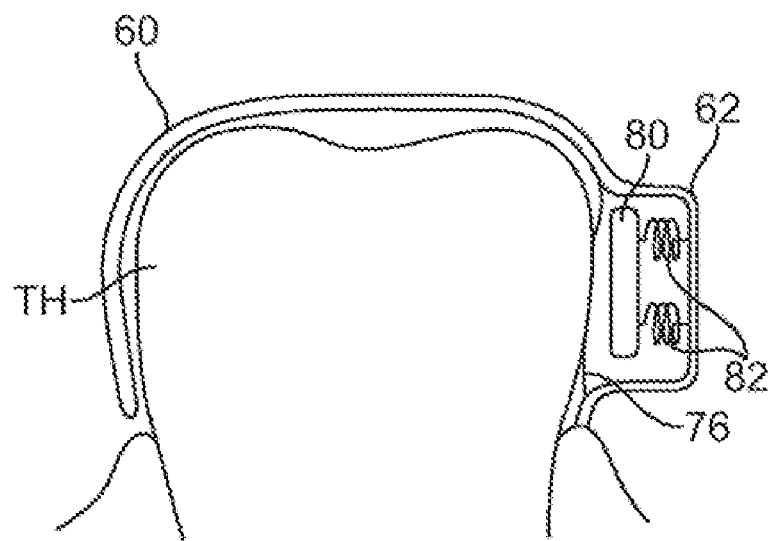
FIG. 8 shows a partial cross-sectional view of another variation of an oral appliance placed upon a tooth with an electronics/transducer assembly pressed against the tooth surface via one or more biasing elements.

Another variation is shown in FIG. 8, which shows electronics and/or transducer assembly 80 contained within housing 62. In this variation, one or more biasing elements 82, e.g., springs, pre-formed shape memory elements, etc., may be placed between assembly 80 and housing 62 to provide a pressing force on assembly 80 to urge the device against the underlying tooth surface, thereby ensuring mechanical contact.

Figure 9:
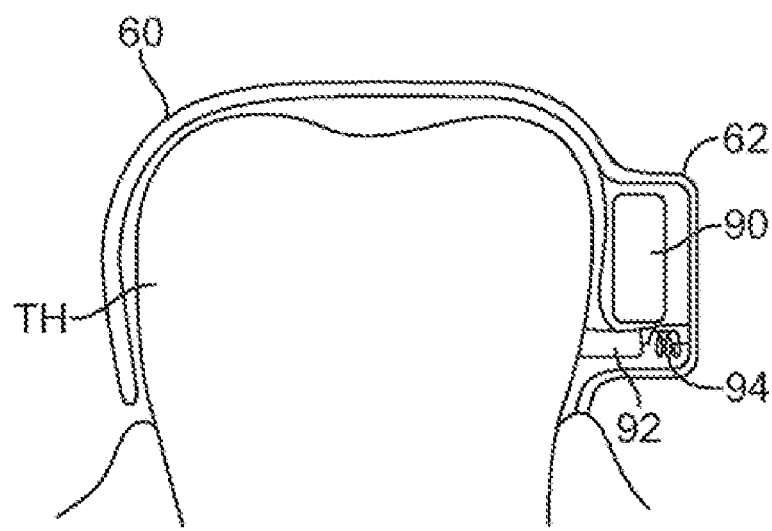
FIG. 9 illustrates another variation of an oral appliance having an electronics assembly and a transducer assembly separated from one another within the electronics and transducer housing of the oral appliance.

In yet another variation, the electronics may be contained as a separate assembly 90 which is encapsulated within housing 62 and the transducer 92 may be maintained separately from assembly 90 but also within housing 62. As shown in FIG. 9, transducer 92 may be urged against the tooth surface via a spring or other biasing element 94 and actuated via any of the mechanisms described above.

Figure 10:
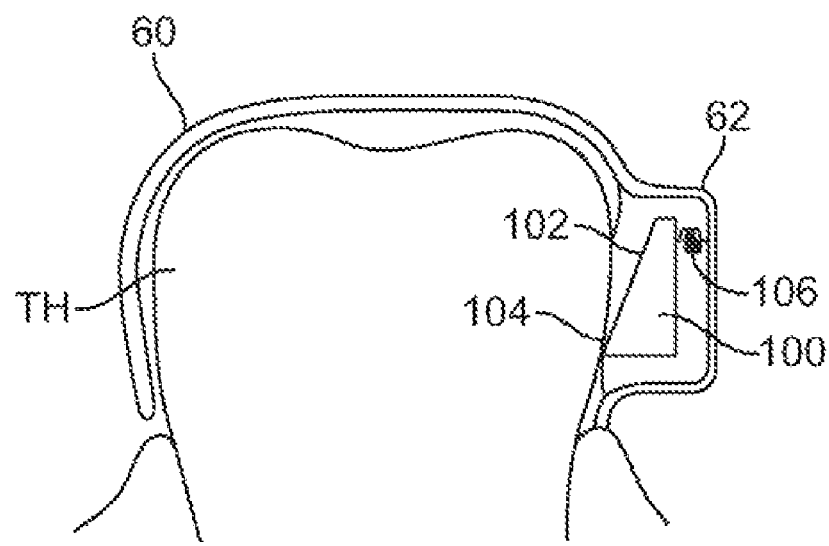
FIGS. 10 and 11 illustrate additional variations of oral appliances in which the electronics and transducer assembly are maintainable against the tooth surface via a ramped surface and a biasing element.

In other variations as shown in FIG. 10, electronics and/or transducer assembly 100 may be configured to have a ramped surface 102 in apposition to the tooth surface. The surface 102 may be angled away from the occlusal surface of the tooth. The assembly 100 may be urged via a biasing element or spring 106 which forces the ramped surface 102 to pivot about a location 104 into contact against the tooth to ensure contact for the transducer against the tooth surface.

Figure 11:
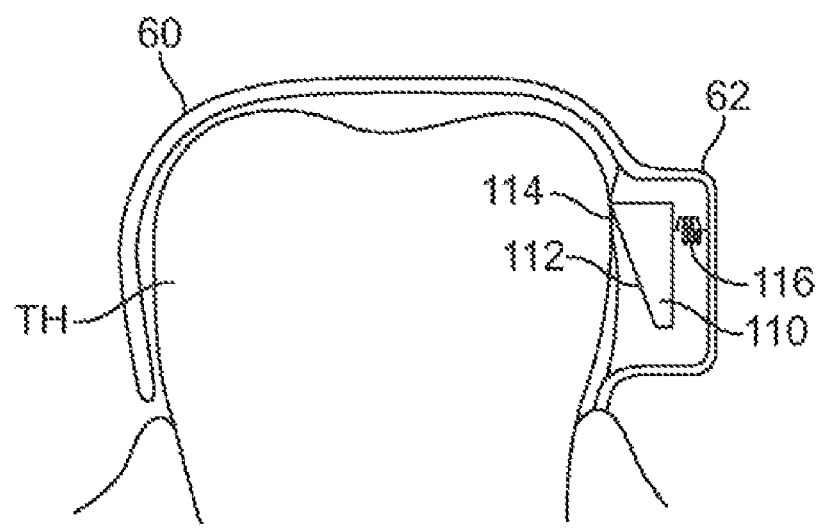

FIG. 11 illustrates another similar variation in electronics and/or transducer assembly 110 also having a ramped surface 112 in apposition to the tooth surface. In this variation, the ramped surface 112 may be angled towards the occlusal surface of the tooth. Likewise, assembly 110 may be urged via a biasing element or spring 116 which urges the assembly 110 to pivot about its lower end such that the assembly 110 contacts the tooth surface at a region 114.

Figure 12:
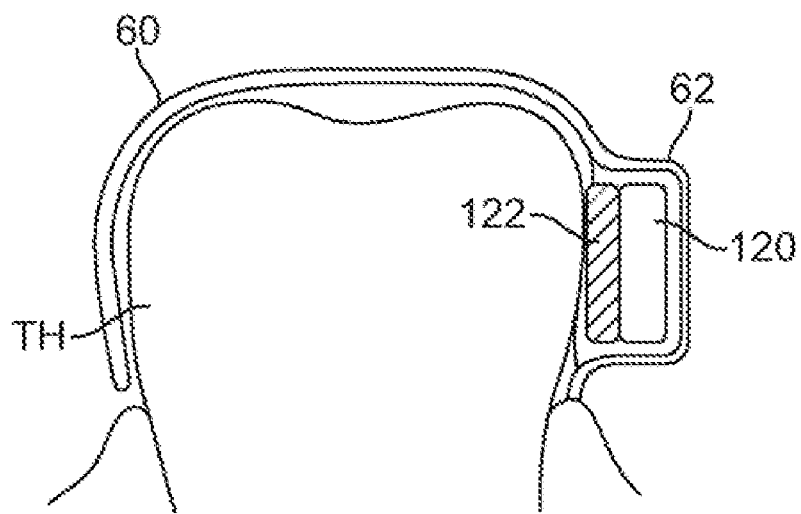
FIG. 12 shows yet another variation of an oral appliance having an interfacing member positioned between the electronics and/or transducer assembly and the tooth surface.

In yet another variation shown in FIG. 12, electronics and/or transducer assembly 120 may be positioned within housing 62 with an interface layer 122 positioned between the assembly 120 and the tooth surface. Interface layer 122 may be configured to conform against the tooth surface and against assembly 120 such that vibrations may be transmitted through layer 122 and to the tooth in a uniform manner. Accordingly, interface layer 122 may be made from a material which attenuates vibrations minimally. Interface layer 122 may be made in a variety of forms, such as a simple insert, an O-ring configuration, etc. or even in a gel or paste form, such as denture or oral paste, etc. Additionally, layer 122 may be fabricated from various materials, e.g., hard plastics or polymeric materials, metals, etc.

Figure 13:
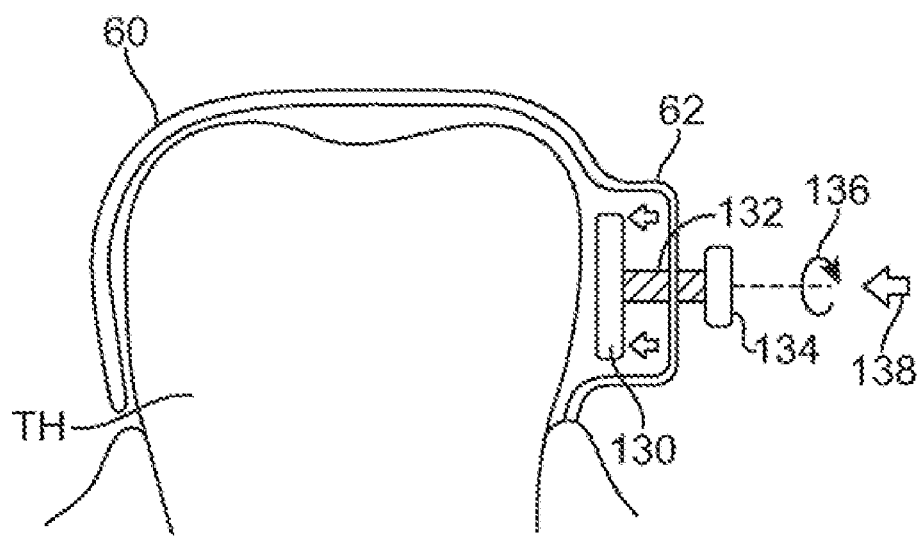
FIG. 13 shows yet another variation of an oral appliance having an actuatable mechanism for urging the electronics and/or transducer assembly against the tooth surface.

FIG. 13 illustrates yet another variation in which electronics and/or transducer assembly 130 may be urged against the tooth surface via a mechanical mechanism. As shown, assembly 130 may be attached to a structural member 132, e.g., a threaded member or a simple shaft, which is connected through housing 62 to an engagement member 134 located outside housing 62. The user may rotate engagement member 134 (as indicated by rotational arrow 136) or simply push upon member 134 (as indicated by linear arrow 138) to urge assembly 130 into contact against the tooth. Moreover, actuation of engagement member 134 may be accomplished manually within the mouth or through the user's cheek or even through manipulation via the user's tongue against engagement member 134.

Figure 14:
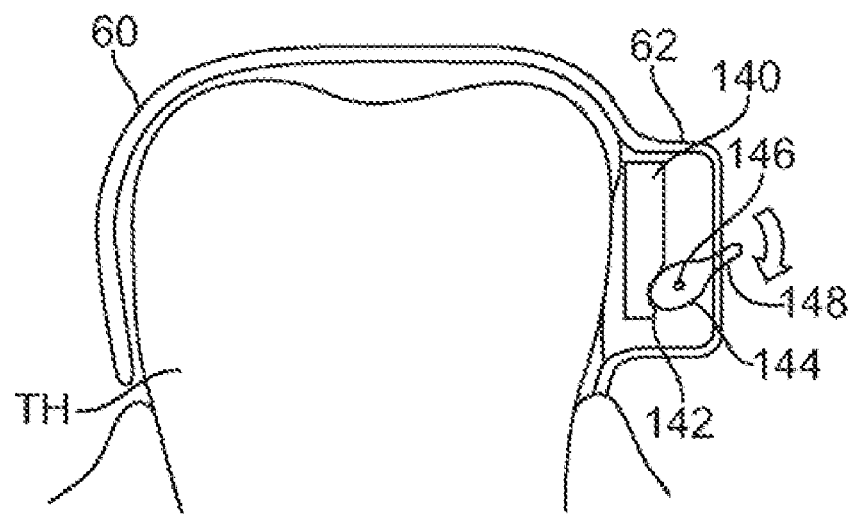
FIG. 14 shows yet another variation of an oral appliance having a cam mechanism for urging the electronics and/or transducer assembly against the tooth surface.

Another variation for a mechanical mechanism is illustrated in FIG. 14. In this variation, electronics and/or transducer assembly 140 may define a portion as an engaging surface 142 for contacting against a cam or lever mechanism 144. Cam or lever mechanism 144 may be configured to pivot 146 such that actuation of a lever 148 extending through housing 62 may urge cam or lever mechanism 144 to push against engaging surface 142 such that assembly 140 is pressed against the underlying tooth surface.

Figure 15:
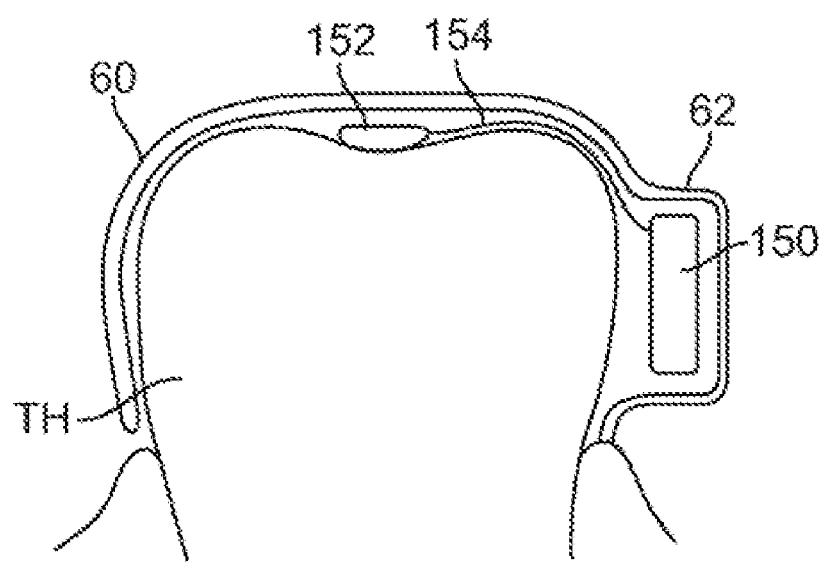
FIG. 15 shows yet another variation of an oral appliance having a separate transducer mechanism positionable upon the occlusal surface of the tooth for transmitting vibrations.

In yet another variation, the electronics 150 and the transducer 152 may be separated from one another such that electronics 150 remain disposed within housing 62 but transducer 152, connected via wire 154, is located beneath dental oral appliance 60 along an occlusal surface of the tooth, as shown in FIG. 15. In such a configuration, vibrations are transmitted via the transducer 152 through the occlusal surface of the tooth. Additionally, the user may bite down upon the oral appliance 60 and transducer 152 to mechanically compress the transducer 152 against the occlusal surface to further enhance the mechanical contact between the transducer 152 and underlying tooth to further facilitate transmission therethrough.

Figure 16:
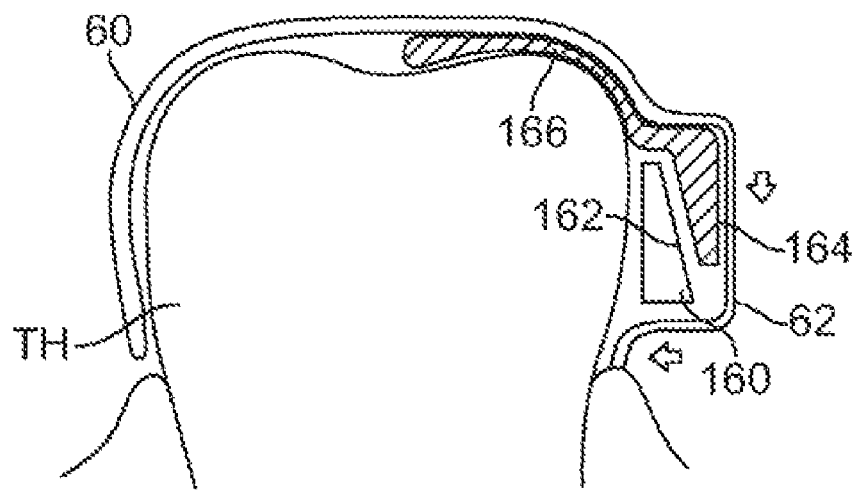
FIG. 16 illustrates another variation of an oral appliance having a mechanism for urging the electronics and/or transducer assembly against the tooth surface utilizing a bite-actuated mechanism.

In the variation of FIG. 16, another example for a bite-enhanced coupling mechanism is illustrated where electronics and/or transducer assembly 160 defines an angled interface surface 162 in apposition to a correspondingly angled engaging member 164. A proximal end of engaging member 164 may extend through housing 62 and terminate in a pusher member 166 positioned over an occlusal surface of the tooth TH. Once oral appliance 60 is initially placed over tooth TH, the user may bite down or otherwise press down upon the top portion of oral appliance 60, thereby pressing down upon pusher member 166 which in turn pushes down upon engaging member 164, as indicated by the arrow. As engaging member 164 is urged downwardly towards the gums, its angled surface may push upon the corresponding and oppositely angled surface 162 to urge assembly 160 against the tooth surface and into a secure mechanical contact.

Figure 17:
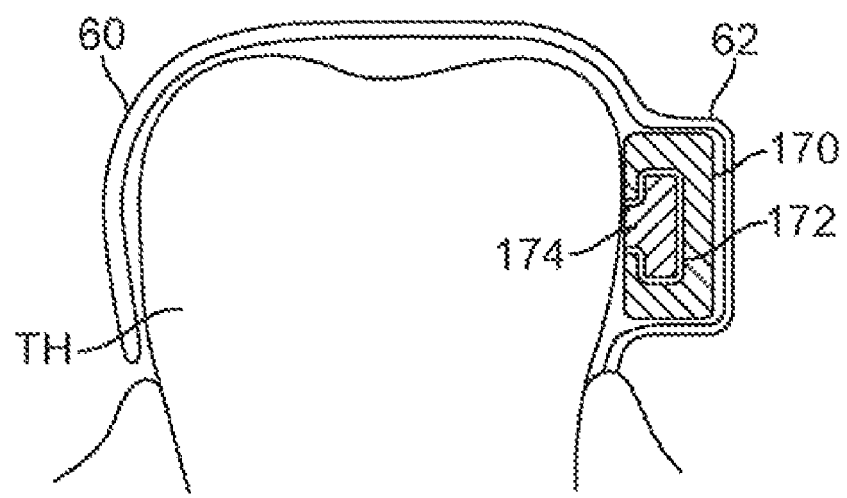
FIG. 17 shows yet another variation of an oral appliance having a composite dental anchor for coupling the transducer to the tooth.

In yet another variation, an electronics and/or transducer assembly 170 may define a channel or groove 172 along a surface for engaging a corresponding dental anchor 174, as shown in FIG. 17. Dental anchor 174 may comprise a light-curable acrylate-based composite material adhered directly to the tooth surface. Moreover dental anchor 174 may be configured in a shape which corresponds to a shape of channel or groove 172 such that the two may be interfitted in a mating engagement. In this manner, the transducer in assembly 170 may vibrate directly against dental anchor 174 which may then transmit these signals directly into the tooth TH.

Figure 18A:
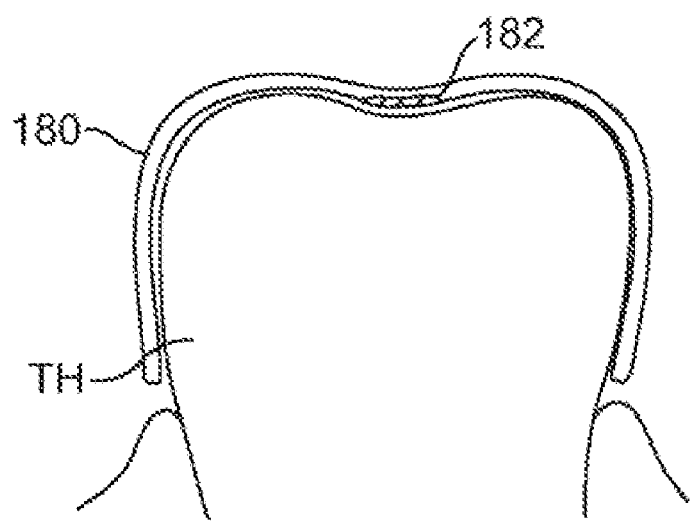
FIGS. 18A and 18B show side and top views, respectively, of an oral appliance; variation having one or more transducers which may be positioned over the occlusal surface of the tooth.
Figure 18B:
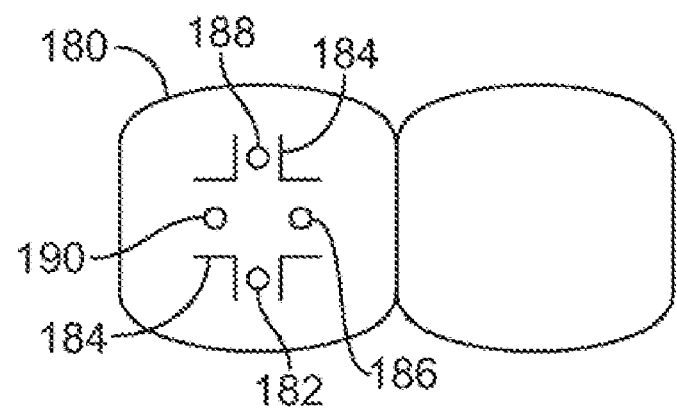

FIGS. 18A and 18B show partial cross-sectional side and top views, respectively, of another variation in which oral appliance 180 may define a number of channels or grooves 184 along a top portion of oral appliance 180. Within these channels or grooves 184, one or more transducers 182, 186, 188, 190 may be disposed such that they are in contact with the occlusal surface of the tooth and each of these transducers may be tuned to transmit frequencies uniformly. Alternatively, each of these transducers may be tuned to transmit only at specified frequency ranges. Accordingly, each transducer can be programmed or preset for a different frequency response such that each transducer may be optimized for a different frequency response and/or transmission to deliver a relatively high-fidelity sound to the user.

Figure 19A:
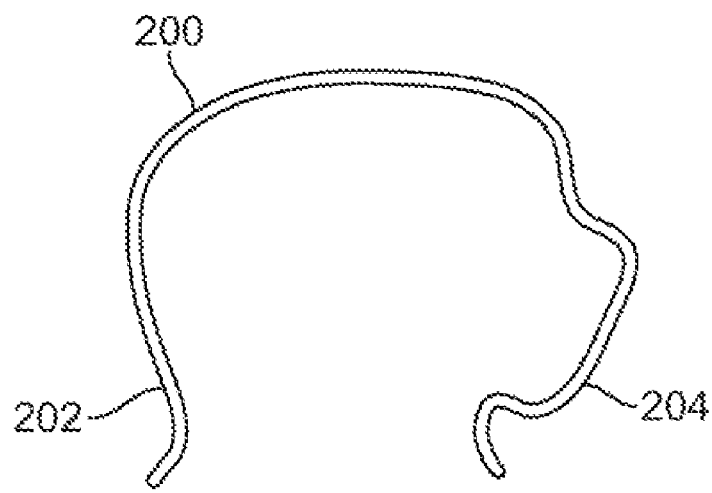
FIGS. 19A and 19B illustrate yet another variation of an oral appliance made from a shape memory material in its pre-formed relaxed configuration and its deformed configuration when placed over or upon the patient's tooth, respectively, to create an interference fit.
Figure 19B:
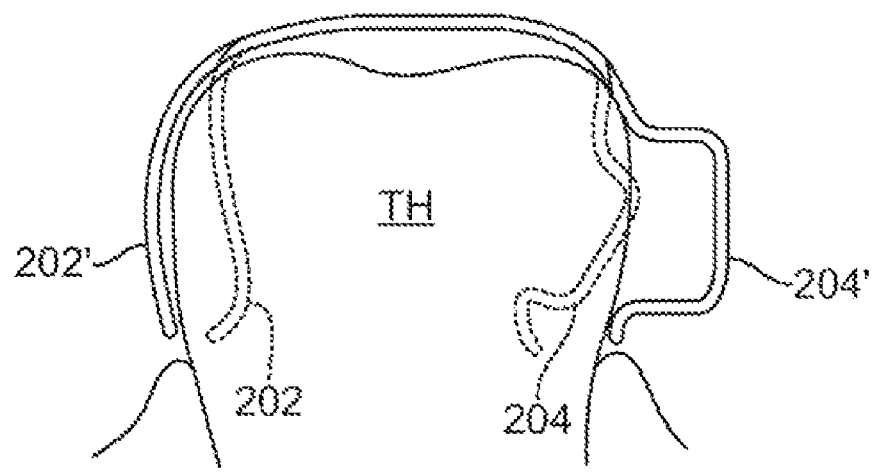

In a yet another variation, FIGS. 19A and 19B illustrate an oral appliance 200 which may be pre-formed from a shape memory polymer or alloy or a superelastic material such as a Nickel-Titanium alloy, e.g., Nitinol. FIG. 19A shows oral appliance 200 in a first configuration where members 202, 204 are in an unbiased memory configuration. When placed upon or against the tooth TH, members 202, 204 may be deflected into a second configuration where members 202', 204' are deformed to engage tooth TH in a secure interference fit, as shown in FIG. 19B. The biased member 204' may be utilized to press the electronics and/or transducer assembly contained therein against the tooth surface as well as to maintain securement of the oral appliance 200 upon the tooth TH.

Figure 20:
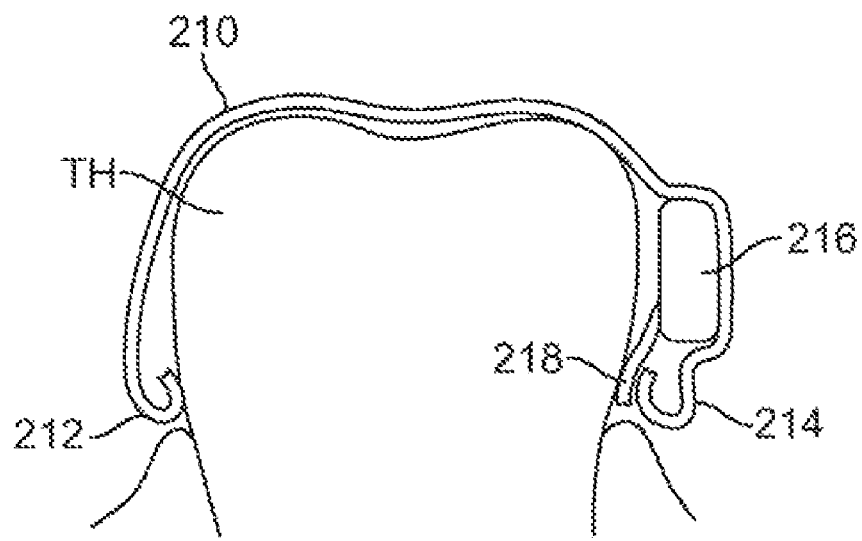
FIG. 20 illustrates yet another variation of an oral appliance made from a pre-formed material in which the transducer may be positioned between the biased side of the oral appliance and the tooth surface.

Similarly, as shown in FIG. 20, removable oral appliance 210 may have biased members to secure engage the tooth TH, as above. In this variation, the ends of the members 212, 214 may be configured into curved portions under which a transducer element 218 coupled to electronics assembly 216 may be wedged or otherwise secured to ensure mechanical contact against the tooth surface.

Figure 21:
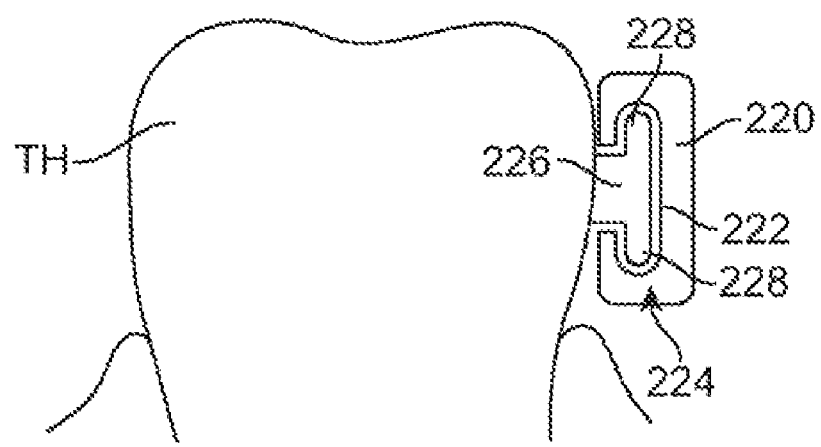
FIG. 21 illustrates a variation in which the oral appliance may be omitted and the electronics and/or transducer assembly may be attached to a composite dental anchor attached directly to the tooth surface.

FIG. 21 shows yet another variation in which the oral appliance is omitted entirely. Here, a composite dental anchor or bracket 226, as described above, may be adhered directly onto the tooth surface. Alternatively, bracket 226 may be comprised of a biocompatible material, e.g., stainless steel, Nickel-Titanium, Nickel, ceramics, composites, etc., formed into a bracket and anchored onto the tooth surface. The bracket 226 may be configured to have a shape 228 over which an electronics and/or transducer assembly 220 may be slid over or upon via a channel 222 having a corresponding receiving configuration 224 for engagement with bracket 226. In this manner, assembly 220 may be directly engaged against bracket 226, through which a transducer may directly vibrate into the underlying tooth TH. Additionally, in the event that assembly 220 is removed from the tooth TH, assembly 220 may be simply slid or rotated off bracket 226 and a replacement assembly may be put in its place upon bracket 226.

Figure 22A:
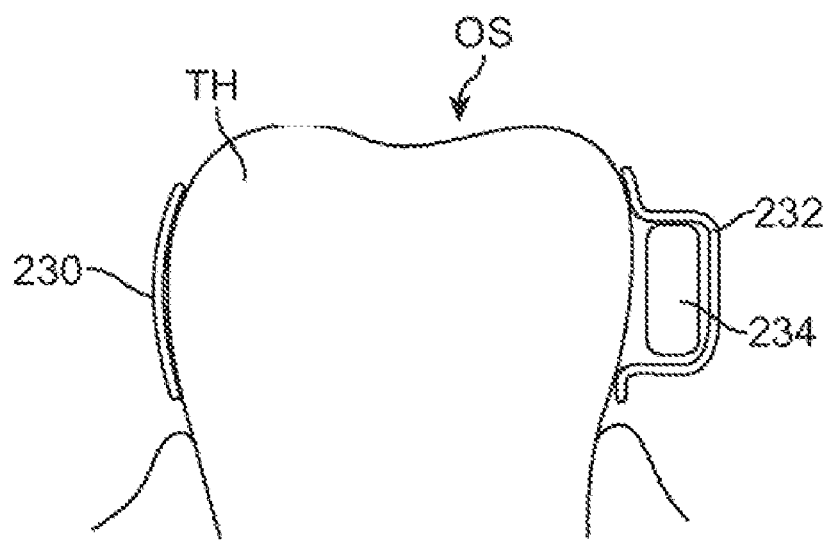
FIGS. 22A and 22B show partial cross-sectional side and perspective views, respectively, of another variation of an oral appliance assembly having its occlusal surface removed or omitted for patient comfort.
Figure 22B:
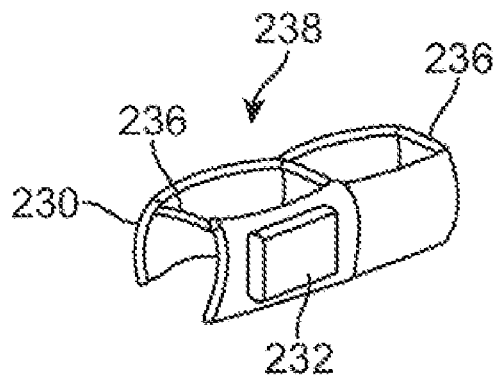

FIGS. 22A and 22B show partial cross-sectional side and perspective views, respectively, of yet another variation of an oral appliance 230. In this variation, the oral appliance 230 may be configured to omit an occlusal surface portion of the oral appliance 230 and instead engages the side surfaces of the tooth TH, such as the lingual and buccal surfaces only. The electronics and/or transducer assembly 234 may be contained, as above, within a housing 232 for contact against the tooth surface. Additionally, as shown in FIG. 22B, one or more optional cross-members 236 may connect the side portions of the oral appliance 230 to provide some structural stability when placed upon the tooth. This variation may define an occlusal surface opening 238 such that when placed upon the tooth, the user may freely bite down directly upon the natural occlusal surface of the tooth unobstructed by the oral appliance device, thereby providing for enhanced comfort to the user.

Figure 23A:
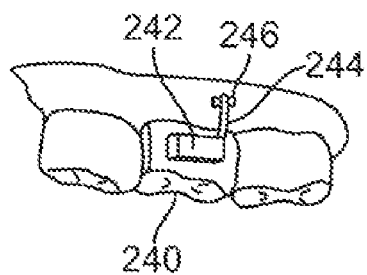
FIGS. 23A and 23B illustrate perspective and side views, respectively, of an oral appliance which may be coupled to a screw or post implanted directly into the underlying bone, such as the maxillary or mandibular bone.
Figure 23B:
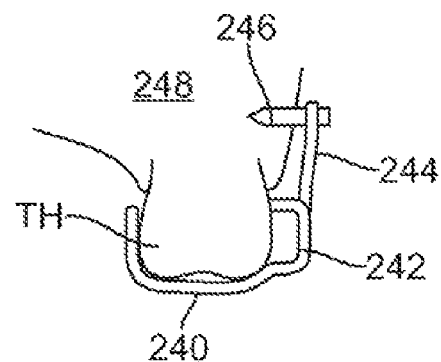

In yet other variations, vibrations may be transmitted directly into the underlying bone or tissue structures rather than transmitting directly through the tooth or teeth of the user. As shown in FIG. 23A, an oral appliance 240 is illustrated positioned upon the user's tooth, in this example upon a molar located along the upper row of teeth. The electronics and/or transducer assembly 242 is shown as being located along the buccal surface of the tooth. Rather than utilizing a transducer in contact with the tooth surface, a conduction transmission member 244, such as a rigid or solid metallic member, may be coupled to the transducer in assembly 242 and extend from oral appliance 240 to a post or screw 246 which is implanted directly into the underlying bone 248, such as the maxillary bone, as shown in the partial cross-sectional view of FIG. 23B. As the distal end of transmission member 244 is coupled directly to post or screw 246, the vibrations generated by the transducer may be transmitted through transmission member 244 and directly into post or screw 246, which in turn transmits the vibrations directly into and through the bone 248 for transmission to the user's inner ear.

Figure 24:
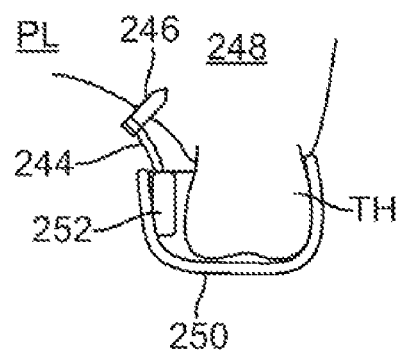
FIG. 24 illustrates another variation in which the oral appliance may be coupled to a screw or post implanted directly into the palate of a patient.

FIG. 24 illustrates a partial cross-sectional view of an oral appliance 250 placed upon the user's tooth TH with the electronics and/or transducer assembly 252 located along the lingual surface of the tooth. Similarly, the vibrations may be transmitted through the conduction transmission member 244 and directly into post or screw 246, which in this example is implanted into the palatine bone PL. Other variations may utilize this arrangement located along the lower row of teeth for transmission to a post or screw 246 drilled into the mandibular bone.

Figure 25A:
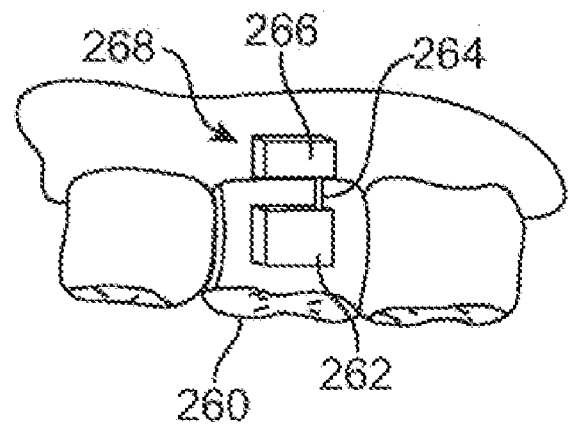
FIGS. 25A and 25B illustrate perspective and side views, respectively, of an oral appliance which may have its transducer assembly or a coupling member attached to the gingival surface to conduct vibrations through the gingival tissue and underlying bone.
Figure 25B:
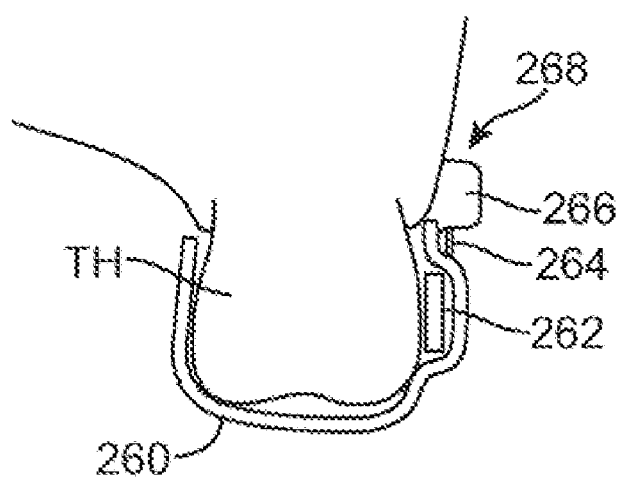

In yet another variation, rather utilizing a post or screw drilled into the underlying bone itself, a transducer may be attached, coupled, or otherwise adhered directly to the gingival tissue surface adjacent to the teeth. As shown in FIGS. 25A and 25B, an oral appliance 260 may have an electronics assembly 262 positioned along its side with an electrical wire 264 extending therefrom to a transducer assembly 266 attached to the gingival tissue surface 268 next to the tooth TH. Transducer assembly 266 may be attached to the tissue surface 268 via an adhesive, structural support arm extending from oral appliance 260, a dental screw or post, or any other structural mechanism. In use, the transducer may vibrate and transmit directly into the underlying gingival tissue, which may conduct the signals to the underlying bone.

Figure 26:
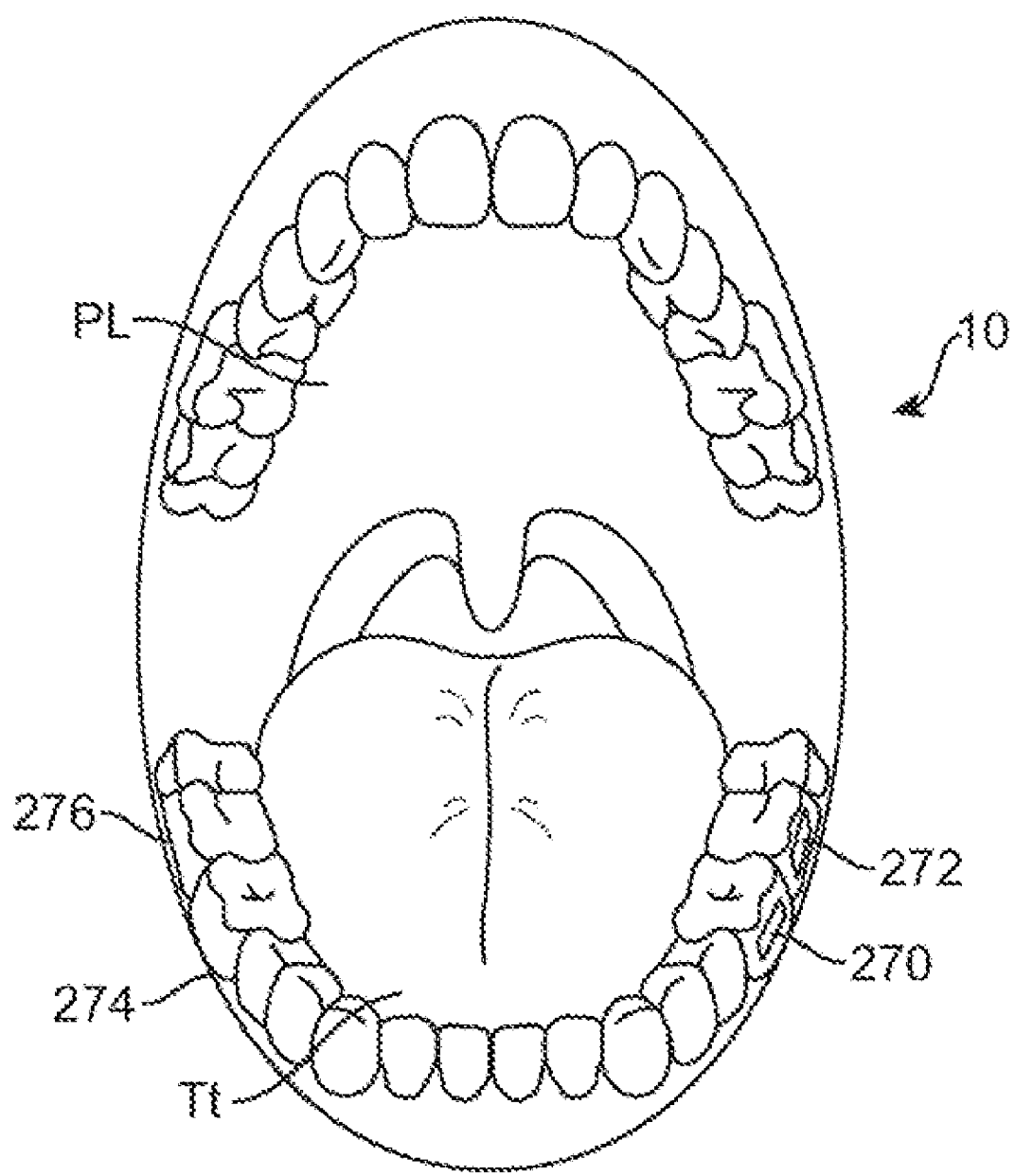
FIG. 26 illustrates an example of how multiple oral appliance two-way communication assemblies or transducers may be placed on multiple teeth throughout the patient's mouth.

For any of the variations described above, they may be utilized as a single device or in combination with any other variation herein, as practicable, to achieve the desired hearing level in the user. Moreover, more than one oral appliance device and electronics and/or transducer assemblies may be utilized at any one time. For example, FIG. 26 illustrates one example where multiple transducer assemblies 270, 272, 274, 276 may be placed on multiple teeth. Although shown on the lower row of teeth, multiple assemblies may alternatively be positioned and located along the upper row of teeth or both rows as well. Moreover, each of the assemblies may be configured to transmit vibrations within a uniform frequency range. Alternatively in other variations, different assemblies may be configured to vibrate within non-overlapping frequency ranges between each assembly. As mentioned above, each transducer 270, 272, 274, 276 can be programmed or preset for a different frequency response such that each transducer may be optimized for a different frequency response and/or transmission to deliver a relatively high-fidelity sound to the user.

Moreover, each of the different transducers 270, 272, 274, 276 can also be programmed to vibrate in a manner which indicates the directionality of sound received by the microphone worn by the user. For example, different transducers positioned at different locations within the user's mouth can vibrate in a specified manner by providing sound or vibrational queues to inform the user which direction a sound was detected relative to an orientation of the user. For instance, a first transducer located, e.g., on a user's left tooth, can be programmed to vibrate for sound detected originating from the user's left side. Similarly, a second transducer located, e.g., on a user's right tooth, can be programmed to vibrate for sound detected originating from the user's right side. Other variations and queues may be utilized as these examples are intended to be illustrative of potential variations.

Figure 27A:
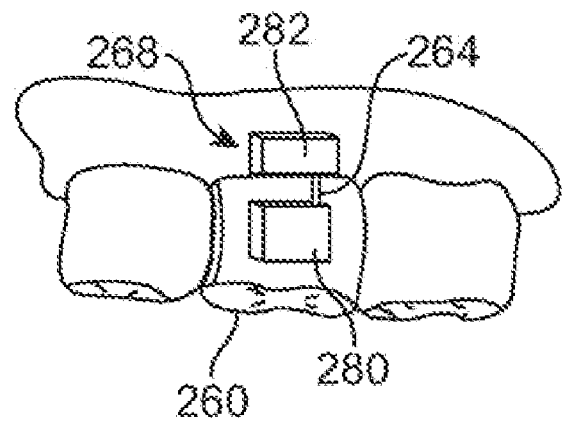
FIGS. 27A and 27B illustrate perspective and side views, respectively, of an oral appliance (similar to a variation shown above) which may have a microphone unit positioned adjacent to or upon the gingival surface to physically separate the microphone from the transducer to attenuate or eliminate feedback.
Figure 27B:
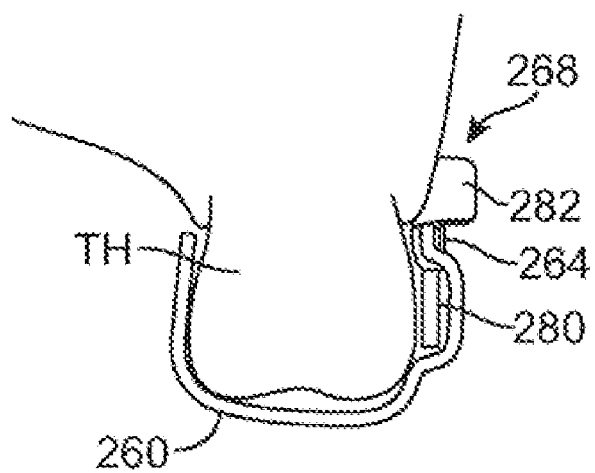

In variations where the one or more microphones are positioned in intra-buccal locations, the microphone may be integrated directly into the electronics and/or transducer assembly, as described above. However, in additional variation, the microphone unit may be positioned at a distance from the transducer assemblies to minimize feedback. In one example, similar to a variation shown above, microphone unit 282 may be separated from electronics and/or transducer assembly 280, as shown in FIGS. 27A and 27B. In such a variation, the microphone unit 282 positioned upon or adjacent to the gingival surface 268 may be electrically connected via wire(s) 264.

Figure 28:
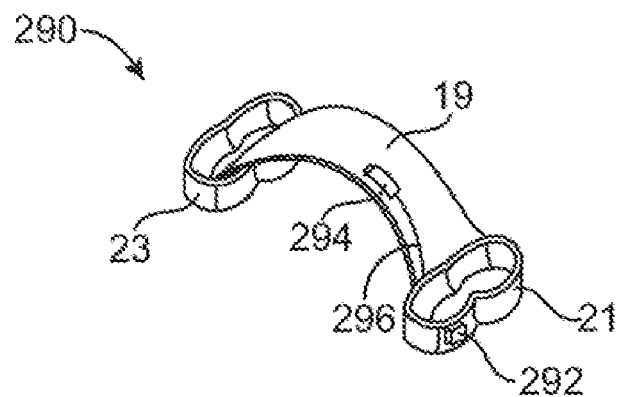
FIG. 28 illustrates another variation of a removable oral appliance supported by an arch and having a microphone unit integrated within the arch.

Although the variation illustrates the microphone unit 282 placed adjacent to the gingival tissue 268, unit 282 may be positioned upon another tooth or another location within the mouth. For instance, FIG. 28 illustrates another variation 290 which utilizes an arch 19 connecting one or more tooth retaining portions 21, 23, as described above. However, in this variation, the microphone unit 294 may be integrated within or upon the arch 19 separated from the transducer assembly 292. One or more wires 296 routed through arch 19 may electrically connect the microphone unit 294 to the assembly 292. Alternatively, rather than utilizing a wire 296, microphone unit 294 and assembly 292 may be wirelessly coupled to one another, as described above.

Figure 29:
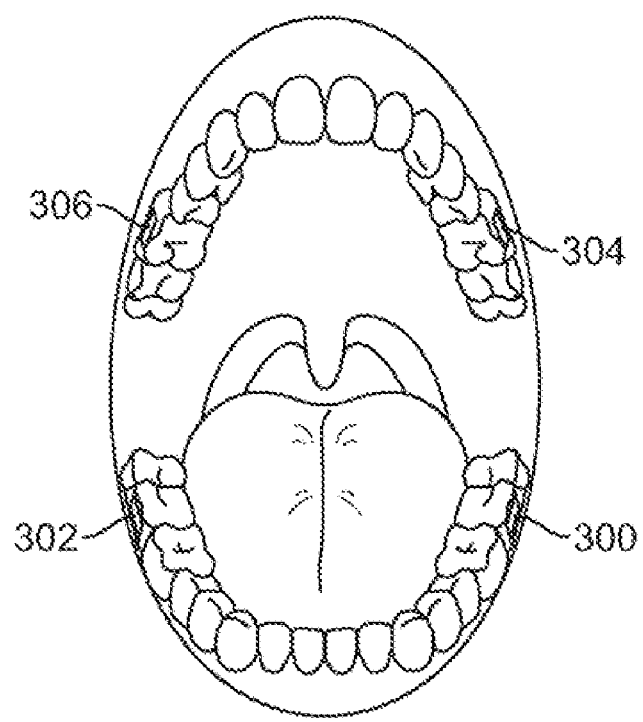
FIG. 29 shows yet another variation illustrating at least one microphone and optionally additional microphone units positioned around the user's mouth and in wireless communication with the electronics and/or transducer assembly.

In yet another variation for separating the microphone from the transducer assembly, FIG. 29 illustrates another variation where at least one microphone 302 (or optionally any number of additional microphones 304, 306) may be positioned within the mouth of the user while physically separated from the electronics and/or transducer assembly 300. In this manner, the one or optionally more microphones 302, 304, 306 may be wirelessly coupled to the electronics and/or transducer assembly 300 in a manner which attenuates or eliminates feedback, if present, from the transducer.

The applications of the devices and methods discussed above are not limited to the treatment of hearing loss but may include any number of further treatment applications. Moreover, such devices and methods may be applied to other treatment sites within the body. Modification of the above-described assemblies and methods for carrying out the invention, combinations between different variations as practicable, and variations of aspects of the invention that are obvious to those of skill in the art are intended to be within the scope of the claims.

What is claimed is:

1. A bone conduction communication apparatus, comprising:
   a housing having a shape which is conformable to at least a portion of at least one tooth of a user;
   a motion sensor to detect a force imposed on the user;
   an actuatable transducer disposed within or upon the housing and in vibratory communication with a surface of the at least one tooth; and
   a wireless satellite transceiver coupled to the motion sensor to communicate the force and coupled to the transducer to provide received sound to the user and to support global communication for the user.

2. The apparatus of claim 1, comprising a protective vest actuated by the motion sensor.

3. The apparatus of claim 1, comprising a protective vest that inflates when the motion sensor detects an incoming force.

4. The apparatus of claim 3, wherein the protective vest is actuated by a blast.

5. The apparatus of claim 3, comprising a helmet.

6. The apparatus of claim 3, comprising a linkage coupling the vest and the helmet, the linkage being hardened when the blast is detected to protect a wearer's neck.

7. The apparatus of claim 1, wherein the housing is uniquely fitted to a person.

8. The apparatus of claim 1, wherein the housing is tamper-proof.

9. The apparatus of claim 1, comprising a controller that disables the communication apparatus when worn by an unauthorized user.

10. The apparatus of claim 1, wherein the motion sensor captures a blast vector comprising direction and magnitude of a blast.

11. The apparatus of claim 10, wherein the blast vector is stored and transmitted to a remote monitoring center.

12. The apparatus of claim 1, wherein the motion sensor comprises an accelerometer.

13. The apparatus of claim 12, wherein the motion sensor comprises a three axis accelerometer.

14. The apparatus of claim 1 wherein the housing comprises an oral appliance having a shape which conforms to the at least one tooth.

15. The apparatus of claim 1 further comprising an electronic assembly disposed within or upon the housing and which is in communication with the transducer.

16. The apparatus of claim 15 wherein the electronic assembly is encapsulated within the housing.

17. The apparatus of claim 15 wherein the electronic assembly further comprises a power supply in electrical communication with transducer.

18. The apparatus of claim 17 wherein the power supply is rechargeable.

19. The apparatus of claim 15 wherein the electronic assembly further comprises a processor in electrical communication with the transducer.

20. The apparatus of claim 15 wherein the electronic assembly further comprises a microphone for receiving auditory signals and which is in electrical communication with the processor.

21. The apparatus of claim 15 wherein the electronic assembly further comprises a receiver in wireless communication with an externally located transmitter assembly.

22. The apparatus of claim 1 wherein the housing is configured as a mouthguard or retainer.

23. The apparatus of claim 1 wherein the housing is adapted to conform to at least the portion of the at least one tooth via an interference fit.

24. The apparatus of claim 1 further comprising:
   a conduction transmission member coupled to the transducer; and
   a post or screw attached to a maxillary or mandibular bone and to the conduction transmission member.

* * * * *